(12) United States Patent
Banet et al.

(10) Patent No.: US 8,419,649 B2
(45) Date of Patent: Apr. 16, 2013

(54) VITAL SIGN MONITOR FOR MEASURING BLOOD PRESSURE USING OPTICAL, ELECTRICAL AND PRESSURE WAVEFORMS

(75) Inventors: Matthew J. Banet, Del Mar, CA (US); Zhou Zhou, San Diego, CA (US); Marshal Singh Dhillon, San Diego, CA (US); Robert J. Kopotic, Jamul, CA (US); Andrew Stanley Terry, San Diego, CA (US); Henk Visser, II, San Diego, CA (US)

(73) Assignee: Sotera Wireless, Inc., San Diego, CA (US)

( * ) Notice: Subject to any disclaimer, the term of this patent is extended or adjusted under 35 U.S.C. 154(b) by 1160 days.

(21) Appl. No.: 12/138,194

(22) Filed: Jun. 12, 2008

(65) Prior Publication Data

US 2009/0018453 A1     Jan. 15, 2009

Related U.S. Application Data

(60) Provisional application No. 60/943,464, filed on Jun. 12, 2007, provisional application No. 60/983,198, filed on Oct. 28, 2007.

(51) Int. Cl.
*A61B 5/02* (2006.01)

(52) U.S. Cl.
USPC .......................................... 600/493; 600/485

(58) Field of Classification Search .................. 600/485, 600/493
See application file for complete search history.

(56) References Cited

U.S. PATENT DOCUMENTS

| | | |
|---|---|---|
| 4,653,498 A | 3/1987 | New, Jr. et al. |
| 5,316,008 A | 5/1994 | Suga et al. |
| 5,649,543 A | 7/1997 | Hosaka et al. |
| 5,857,975 A | 1/1999 | Golub |
| 5,865,755 A | 2/1999 | Golub |
| 6,517,495 B1 | 2/2003 | Hersh |
| 6,719,703 B2 | 4/2004 | Chen et al. |
| 2004/0024324 A1 | 2/2004 | Bratteli |
| 2004/0193068 A1 | 9/2004 | Burton et al. |
| 2005/0216199 A1 | 9/2005 | Banet |
| 2005/0228296 A1 | 10/2005 | Banet |
| 2005/0228298 A1 | 10/2005 | Banet et al. |
| 2005/0228299 A1 | 10/2005 | Banet |
| 2005/0228300 A1 | 10/2005 | Jaime et al. |
| 2005/0228301 A1 | 10/2005 | Banet et al. |
| 2006/0247538 A1 | 11/2006 | Davis |
| 2007/0142715 A1 | 6/2007 | Banet et al. |
| 2007/0185393 A1 | 8/2007 | Zhou et al. |
| 2007/0276261 A1 | 11/2007 | Banet et al. |
| 2007/0276632 A1 | 11/2007 | Banet et al. |
| 2008/0082004 A1 | 4/2008 | Banet et al. |
| 2008/0221399 A1 | 9/2008 | Zhou et al. |

FOREIGN PATENT DOCUMENTS

WO     WO-03/084396     10/2003

OTHER PUBLICATIONS

Chemla, et al., "Mean Aortic Pressure is the Geometric Mean of Systolic and Diastolic Aortic Pressure in Resting Humans," J. Appl. Physiol., 99:2278-2284, 2005, 8 pages.

Zong, et al., "Effects of Vasoactive Drugs on the Relationship between ECG-pulse Wave Delay Time and Arterial Blood Pressure in ICU Patients," IEEE, Computers in Cardiology, 1998, vol. 25, 4 pages.

International Search Report and Written Opinion, International Patent Application No. PCT/US08/66769, mailed Oct. 22, 2008 (13 pages).

*Primary Examiner* — J. E. Angell

(74) *Attorney, Agent, or Firm* — Michael A. Whittaker; Acuity Law Group, P.C.

(57) ABSTRACT

A method and apparatus for continuous measurement of blood pressure, based on pulse transit time, which does not require any external calibration. This technique, referred to herein as the 'composite technique', is carried out with a body-won sensor that measures blood pressure and other vital signs, and wirelessly transmits them to a remote monitor. A network of disposable sensors, typically placed on the patient's right arm and chest, connect to the body sensor and measure a time-dependent electrical waveform, optical waveform, and pressure waveform. The disposable sensors typically include an armband that features an inflatable bladder coupled to a pressure sensor, at least 3 electrical sensors (e.g. electrodes), and an optical sensor (e.g., a light source and photodiode) attached to a wrist-worn band.

11 Claims, 25 Drawing Sheets

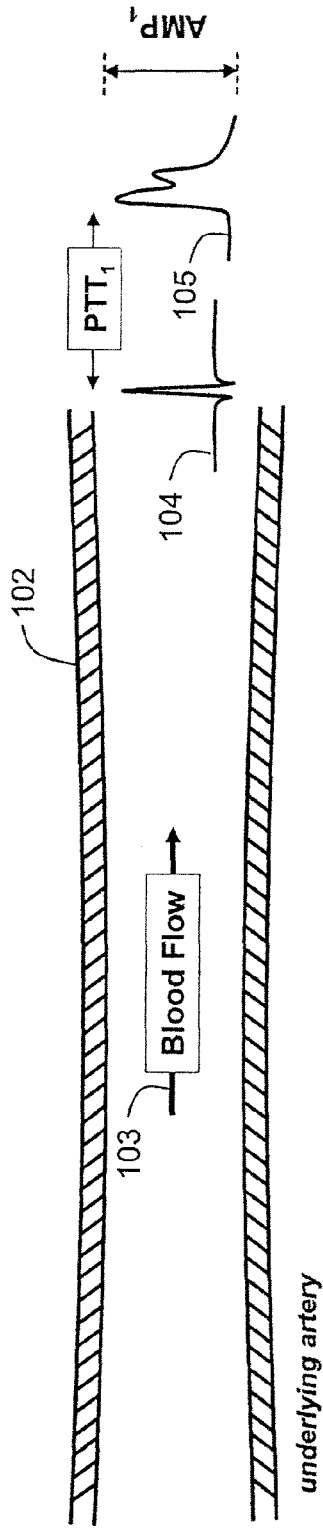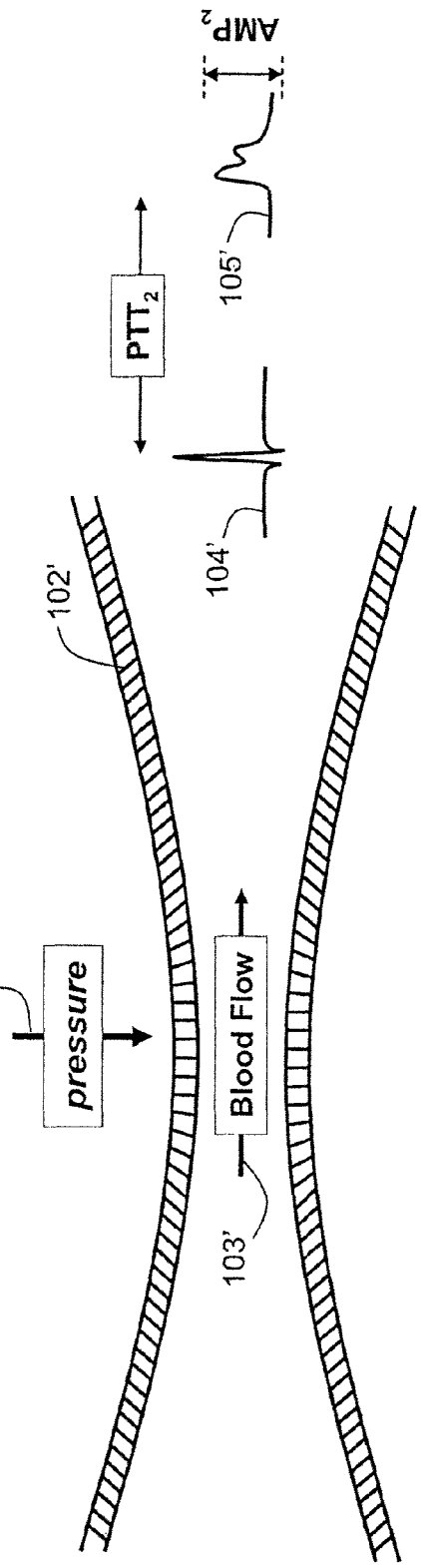
Fig. 1A
Fig. 1B

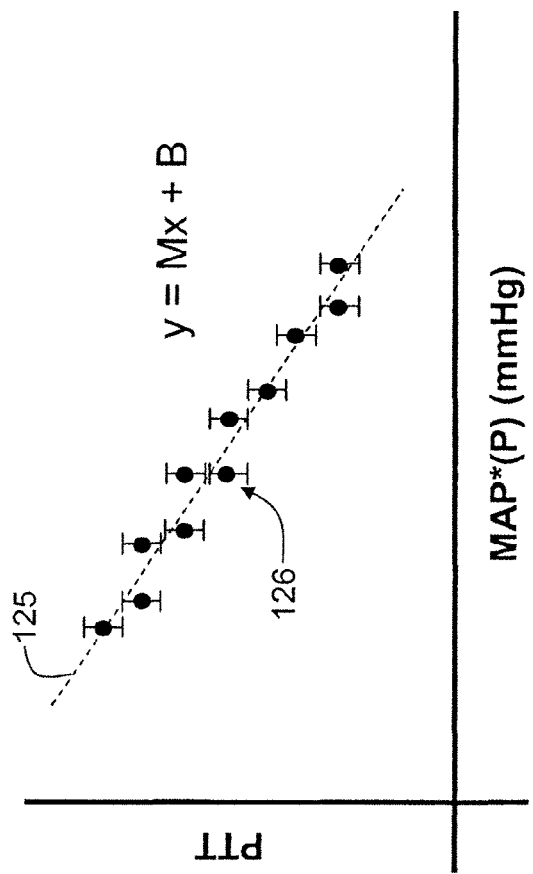
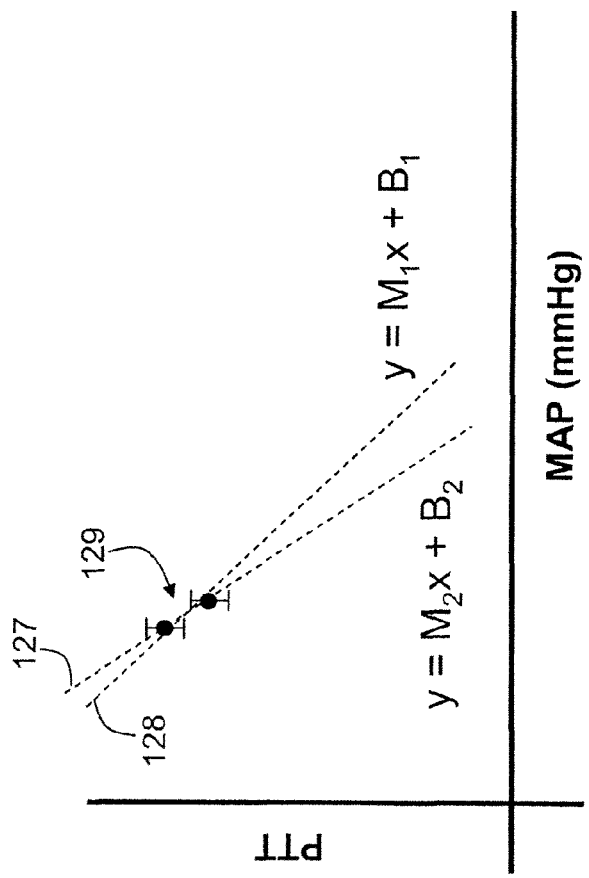

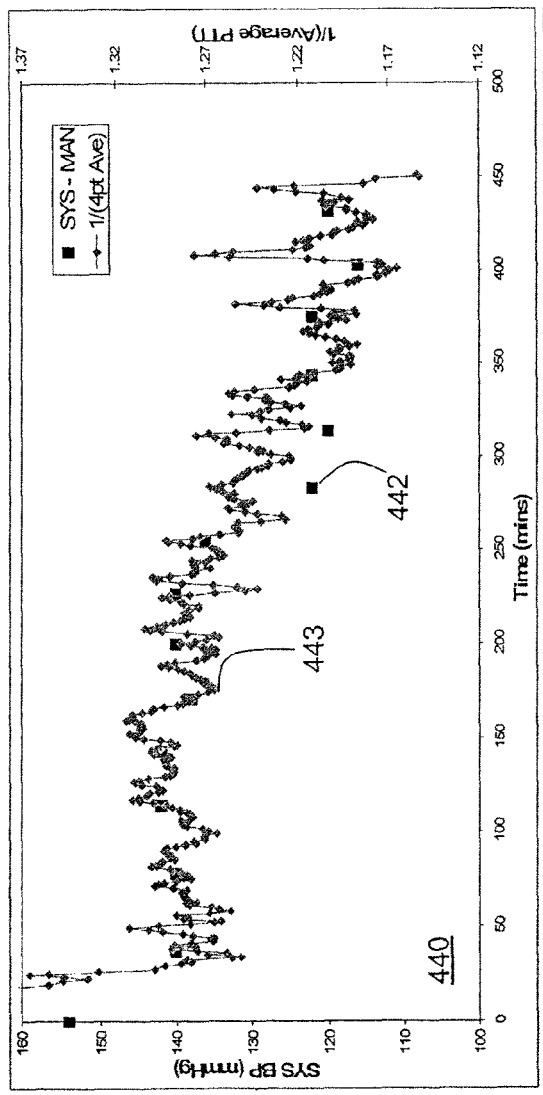
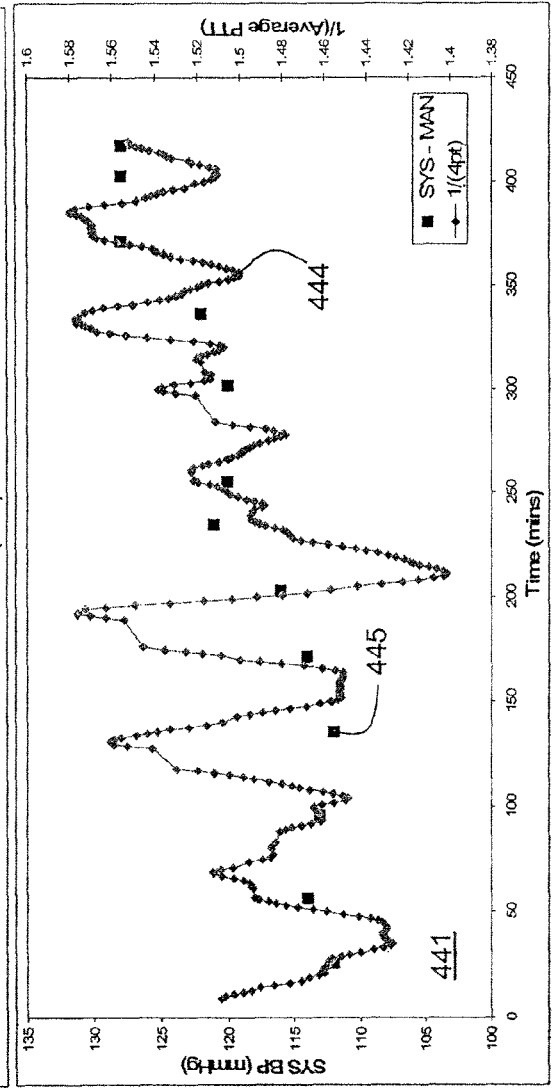
Fig. 19A
Fig. 19B

VITAL SIGN MONITOR FOR MEASURING BLOOD PRESSURE USING OPTICAL, ELECTRICAL AND PRESSURE WAVEFORMS

CROSS-REFERENCE TO RELATED APPLICATIONS

This application claims the benefit of U.S. Provisional Application No. 60/943,464; filed Jun. 12, 2007, and U.S. Provisional Application No. 60/983,198, filed Oct. 28, 2007, all of which are incorporated herein by reference.

FIELD OF THE INVENTION

The present invention generally relates to medical devices for monitoring vital signs, e.g., arterial blood pressure.

BACKGROUND OF THE INVENTION

Pulse transit time (PTT), defined as the transit time for a pressure pulse launched by a heartbeat in a patient's arterial system, has been shown in a number of studies to correlate to both systolic and diastolic blood pressure. In these studies, PTT is typically measured with a conventional vital signs monitor that includes separate modules to determine both an electrocardiogram (ECG) and pulse oximetry. During a PTT measurement, multiple electrodes typically attach to a patient's chest to determine a time-dependent ECG component characterized by a sharp spike called the 'QRS complex'. The QRS complex indicates an initial depolarization of ventricles within the heart and, informally, marks the beginning of the heartbeat and a pressure pulse that follows. Pulse oximetry is typically measured with a bandage or clothespin-shaped sensor that attaches to a patient's finger, and includes optical systems operating in both the red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation measured by the photodetector to determine the patient's blood oxygen saturation level and a time-dependent waveform called a photoplethysmograph ('PPG'). Time-dependent features of the optical waveform indicate both pulse rate and a volumetric absorbance change in an underlying artery (e.g., in the finger) caused by the propagating pressure pulse.

Typical PTT measurements determine the time separating a maximum point on the QRS complex (indicating the peak of ventricular depolarization) and a foot of the optical waveform (indicating the beginning the pressure pulse). PTT depends primarily on arterial compliance, the propagation distance of the pressure pulse (which is closely approximated by the patient's arm length), and blood pressure. To account for patient-dependent properties, such as arterial compliance, PTT-based measurements of blood pressure are typically 'calibrated' using a conventional blood pressure cuff. Typically during the calibration process the blood pressure cuff is applied to the patient, used to make one or more blood pressure measurements, and then removed. Going forward, the calibration blood pressure measurements are used, along with a change in PTT, to determine the patient's blood pressure and blood pressure variability. PTT typically relates inversely to blood pressure, i.e., a decrease in PTT indicates an increase in blood pressure.

A number of issued U.S. patents describe the relationship between PTT and blood pressure. For example, U.S. Pat. Nos. 5,316,008; 5,857,975; 5,865,755; and 5,649,543 each describe an apparatus that includes conventional sensors that measure an ECG and optical waveform, which are then processed to determine PTT.

SUMMARY OF THE INVENTION

Embodiments described herein provides a technique for continuous measurement of blood pressure, based on PTT, which does not require any external calibration. This technique, referred to herein as the 'composite technique', is carried out with a body-worn sensor (referred to herein as the 'body sensor') that measures blood pressure and other vital signs, and wirelessly transmits them to a remote monitor (referred to herein as the 'monitor'). A network of disposable sensors, typically placed on the patient's right arm and chest, connect to the body sensor and measure a time-dependent ECG (referred to herein as an 'electrical waveform'), PPG (referred to herein as an 'optical waveform'), and pressure waveform. These disposable sensors typically include an armband that features an inflatable air bladder coupled to a pressure sensor, at least 3 electrical sensors (e.g. ECG electrodes), and an optical sensor (e.g., a light source and photodiode) attached to a wrist-worn band. These sensors connect to the body sensor using disposable cables, and are typically discarded after use. The sensors measure the optical, electrical, and pressure waveforms, which the body sensor then processes according to the composite technique to determine blood pressure and other vital signs. The body sensor then wirelessly transmits this information (typically using a two-way wireless protocol, e.g. Bluetooth) to the monitor. The monitor displays both vital signs and the time-dependent optical, electrical, and pressure waveforms. The monitor additionally includes a barcode scanner, touchscreen display, removable memory, and wireless modems that operate with both local-area networks (e.g. 802.11 or 'WiFi' networks) and wide-area networks (e.g. the Sprint network) to transmit information to external computer systems.

The composite technique includes both pressure-dependent and pressure-free measurements. It is based on the realization that PTT and the optical waveform used to determine it are strongly modulated by an applied pressure. Two events occur as the pressure gradually increases to the patient's systolic pressure: 1) PTT increases in a non-linear manner once the applied pressure exceeds diastolic pressure; and 2) the magnitude of the PPG's amplitude systematically decreases, typically in a linear manner, as the applied pressure approaches systolic pressure. The applied pressure gradually decreases blood flow and consequent blood pressure in the patient's arm, and therefore induces the pressure-dependent increase in PTT. Each of the resulting pairs of PTT/blood pressure readings measured during the period of applied pressure can be used as a calibration point. Moreover, when the applied pressure equals systolic blood pressure, the amplitude of the optical waveform is completely eliminated, and PTT is no longer measurable. In total, analyzing both PTT and the optical waveform's amplitude over a suitable range yields the patient's systolic and diastolic blood pressures. The composite technique measures systolic blood pressure directly; in contrast, conventional cuff-based systems based on the oscillometric technique measure this property indirectly, which is typically less accurate.

In addition, the composite technique can include an 'intermediate' pressure-dependent measurement wherein the armband is partially inflated. This partially decreases the amplitude of the optical waveform in a time-dependent manner. The amplitude's pressure-dependent decrease can then be 'fit' with a numerical function to estimate the pressure at which the amplitude completely disappears, indicating systolic pressure.

For the pressure-dependent measurement, a small mechanical pump in the body sensor inflates the bladder to apply pressure to an underlying artery according to the pressure waveform. The armband is typically located on the patient's upper arm, proximal to the brachial artery, and time-dependent pressure is measured by an internal pressure sensor in the body sensor. The pressure sensor is typically an in-line Wheatstone bridge or strain gauge. The pressure waveform gradually ramps up in a mostly linear manner during inflation, and then slowly deflates through a 'bleeder valve' during deflation. During inflation, mechanical pulsations corresponding to the patient's heartbeats couple into the bladder as the applied pressure approaches diastolic pressure. The mechanical pulsations modulate the pressure waveform so that it includes a series of time-dependent oscillations. The oscillations are similar to those measured with an automated blood pressure cuff using the oscillometric technique, only they are measured during inflation rather than deflation. They are processed as described below to determine mean arterial pressure, which is then used going forward in the pressure-free measurement. Specifically, the maximum amplitude of the pulsations corresponds to mean arterial pressure; measuring this property from the pressure waveform represents a direct measurement. Once determined, direct measurements of systolic and mean arterial pressure made during the pressure-dependent measurement are used to determine diastolic pressure using a numerical calculation, described in more detail below.

Pressure-free measurements immediately follow the pressure-dependent measurements, and are typically made by determining PTT with the same optical and electrical sensors used in the pressure-dependent measurements. Specifically, the body sensor processes PTT and other properties of the optical waveform, along with the measurements of systolic, diastolic, and mean arterial pressure made during the pressure-dependent measurement, to determine blood pressure.

In addition to blood pressure, the body sensor measures heart rate and respiratory rate from components of the electrical waveform. These measurements are made using conventional algorithms. An optional wrist-worn pulse oximeter measures SpO2 and transmits this through a wireless interface (e.g. Bluetooth) to the monitor. The body sensor can also measure temperature and patient motion with additional sensors (e.g. a thermocouple and accelerometer), and respiratory rate with a chest-worn acoustic sensor integrated with one of the electrodes used to measure the electrical waveform.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 1A and 1B show, respectively, schematics drawings indicating the composite technique's pressure-dependent and pressure-free measurements.

FIG. 5A shows a graph of PTT as a function of 'effective' mean arterial blood pressure (MAP*(P)) determined using the pressure-dependent measurement of the composite technique.

FIG. 5B shows a graph of PTT as a function of mean arterial blood pressure (MAP) determined using a conventional blood pressure measurement of the prior art.

FIGS. 19A and 19B are time-dependent graphs of systolic blood pressure measured with the pressure-dependent and pressure-free measurements of the composite technique and a manual measurement for, respectively, two patients undergoing dialysis.

DETAILED DESCRIPTION

Figure 2:
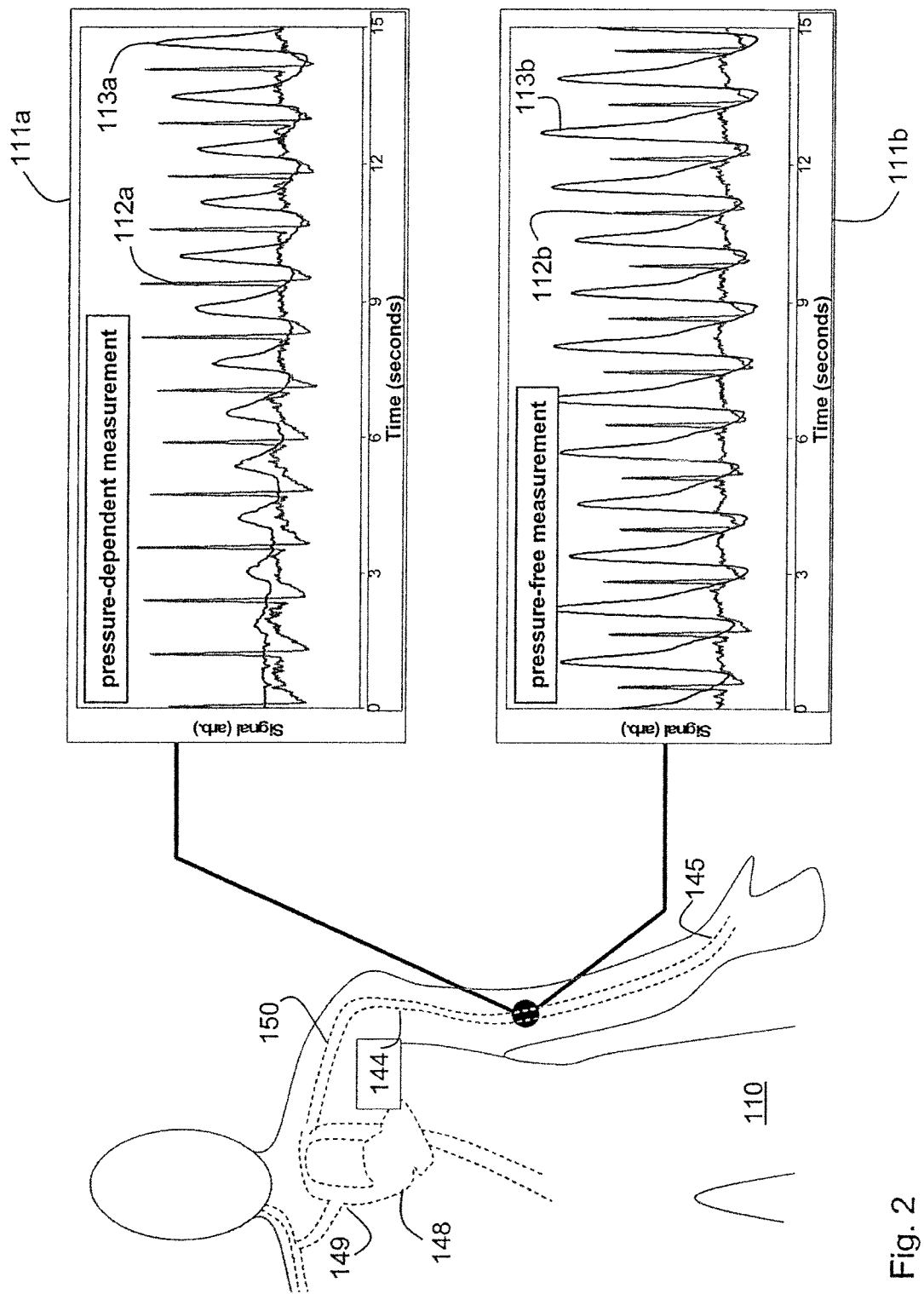
FIG. 2 shows a schematic drawing of a patient and optical and electrical waveforms measured during the pressure-dependent and pressure-free measurements of FIGS. 1A and 1B.

FIGS. 1A and 1B show schematic drawings of the composite technique's pressure-free (FIG. 1A) and pressure-dependent (FIG. 1B) measurements. Working in concert, these measurements accurately and continuously determine the patient's blood pressure for an extended time without requiring an external calibration device, e.g., a conventional blood pressure cuff. During a measurement, the patient wears a body sensor attached to a disposable armband and optical and electrical sensors. These sensors measure signals for both the pressure-dependent and pressure-free measurements. The co-pending patent applications, entitled: DEVICE AND METHOD FOR DETERMINING BLOOD PRESSURE USING 'HYBRID' PULSE TRANSIT TIME MEASUREMENT (U.S. Ser. No. 60/943,464; filed Jun. 12, 2007); and, VITAL SIGN MONITOR FOR CUFFLESSLY MEASURING BLOOD PRESSURE USING A PULSE TRANSIT TIME CORRECTED FOR VASCULAR INDEX (U.S. Ser. No. 60/943,523; filed Jun. 12, 2007), describe these components in more detail and are incorporated herein by reference. A microprocessor in the body sensor processes the optical and electrical waveforms to determine PTT, which is used in both measurements of the composite technique to determine blood pressure, as is described in more detail below.

The armband includes an air bladder which, when pressurized with a mechanical pump, applies a pressure 107 to an underlying artery 102, 102'. An electrical system featuring at least 3 electrodes coupled to an amplifier/filter circuit within the body sensor measures an electrical waveform 104, 104' from the patient. Three electrodes (two detecting positive and negative signals, and one serving as a ground) are typically required to detect the necessary signals to generate an electrical waveform with an adequate signal-to-noise ratio. At the same time, an optical system featuring a reflective optical sensor measures an optical waveform 105, 105' featuring a series of 'pulses', each characterized by an amplitude of $AMP_1$, $AMP_2$, from the patient's artery. A good measurement site is typically proximal to the brachial or radial arteries, or the smaller arteries near the base of the thumb on the palm side of the hand. A microprocessor and analog-to-digital converter within the body sensor detects and analyzes the electrical 104, 104' and optical 105, 105' waveforms to determine both $PTT_1$ (from the pressure-free measurement) and $PTT_2$ (from the pressure-dependent measurement). Typically the microprocessor determines both $PTT_1$ and $PTT_2$ by calculating the time difference between the peak of the QRS complex in the electrical waveform 104, 104' and the foot (i.e. onset) of the optical waveform 105, 105'.

Embodiments described herein are based at least in part on the recognition that an applied pressure (indicated by arrow 107) during the pressure-dependent measurement affects blood flow (indicated by arrows 103, 103') in the underlying artery 102, 102'. Specifically, the applied pressure has no affect on either $PTT_2$ or $AMP_2$ when it is less than a diastolic pressure within the artery 102, 102'. When the applied pressure 107 reaches the diastolic pressure it begins to compress the artery, thus reducing blood flow and the effective internal pressure. This causes $PTT_2$ to systematically increase relative to $PTT_1$, and $AMP_2$ to systematically decrease relative to $AMP_1$. $PTT_2$ increases and $AMP_2$ decreases (typically in a linear manner) as the applied pressure 107 approaches the systolic blood pressure within the artery 102, 102'. When the applied pressure 107 reaches the systolic blood pressure, $AMP_2$ is completely eliminated and $PTT_2$ consequently becomes immeasurable.

FIG. 2 illustrates the above-mentioned measurement in more detail. During a measurement the patient's heart 148 generates electrical impulses that pass through the body near the speed of light. These impulses accompany each heart beat, which then generates a pressure wave that propagates through the patient's vasculature at a significantly slower speed. Immediately after the heartbeat, the pressure wave leaves the heart 148 and aorta 149, passes through the subclavian artery 150, to the brachial artery 144, and from there through the radial and ulnar arteries 145 to smaller arteries in the patient's fingers. Three disposable electrodes located on the patient's chest measure unique electrical signals which pass to an amplifier/filter circuit within the body sensor. Typically, these electrodes attach to the patient's chest in a 1-vector 'Einthoven's triangle' configuration to measure unique electrical signals. Within the body sensor, the signals are processed using the amplifier/filter circuit to determine an analog electrical signal, which is digitized with an analog-to-digital converter to form the electrical waveform and then stored in memory. The optical sensor typically includes an optical module featuring an integrated photodetector, amplifier, and pair of light sources operating near 570 nm. This wavelength is selected because it is particularly sensitive to volumetric absorbance changes in an underlying artery for a wide variety of skin types when deployed in a reflection-mode geometry, as described in the following co-pending patent application, the entire contents of which are incorporated herein by reference: SYSTEM FOR MEASURING VITAL SIGNS USING AN OPTICAL MODULE FEATURING A GREEN LIGHT SOURCE (U.S. Ser. No. 11/307,375; filed Feb. 3, 2006). The optical sensor detects reflected radiation, which is further processed with a second amplifier/filter circuit within the body sensor. This results in the optical waveform, which, as described above, includes a series of pulses, each corresponding to an individual heartbeat. A second optical sensor can also be used to measure a second optical waveform from one of these arteries.

During the composite technique, the same optical and electrical sensors are used during the pressure-dependent and pressure-free measurements to measure signals from the patient 110. Optical 113a, 113b and electrical 112a, 112b waveforms from these measurements are shown in the graphs 111a, 111b in the figure. In the top graph showing the pressure-dependent measurement pressure gradually decreases with time.

Each pulse in the optical waveforms 113a, 113b from both measurements corresponds to an individual heartbeat, and represents a volumetric absorbance change in an underlying artery caused by the propagating pressure pulse. Likewise, the electrical waveforms 112a, 112b from each measurement feature a series of sharp, 'QRS' complexes corresponding to each heartbeat. As described above, pressure has a strong impact on amplitudes of pulses in the optical waveform 113a during the pressure-dependent measurement, but has no impact on the amplitudes of QRS complexes in the corresponding electrical waveform 112a. These waveforms are processed as described below to determine blood pressure.

Figure 3:
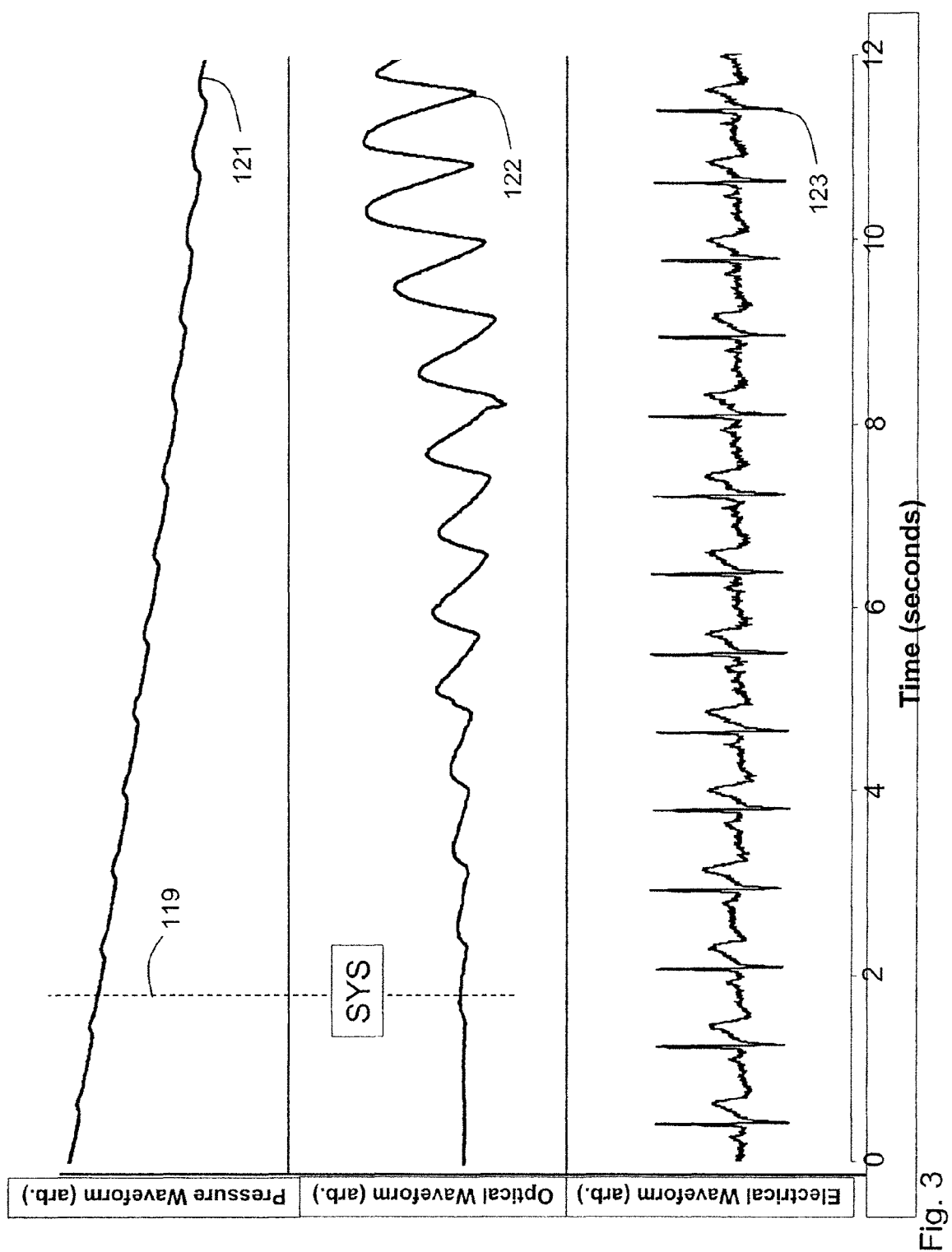
FIG. 3 shows graphs of time-dependent pressure, optical, and electrical waveforms measured with the body sensor and disposable sensors.
Figure 4A:
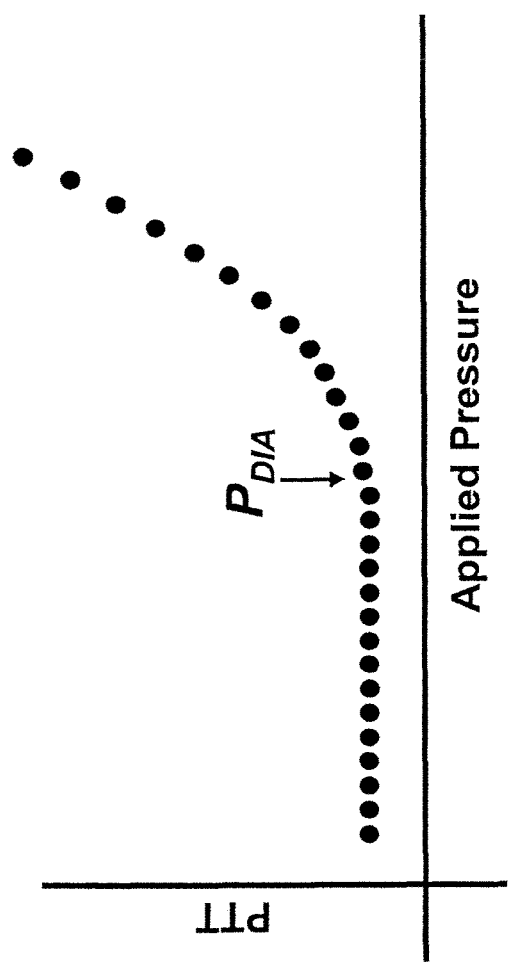
FIGS. 4A and 4B show graphs of, respectively, PTT and the amplitude of the optical waveform as a function of pressure.
Figure 4B:
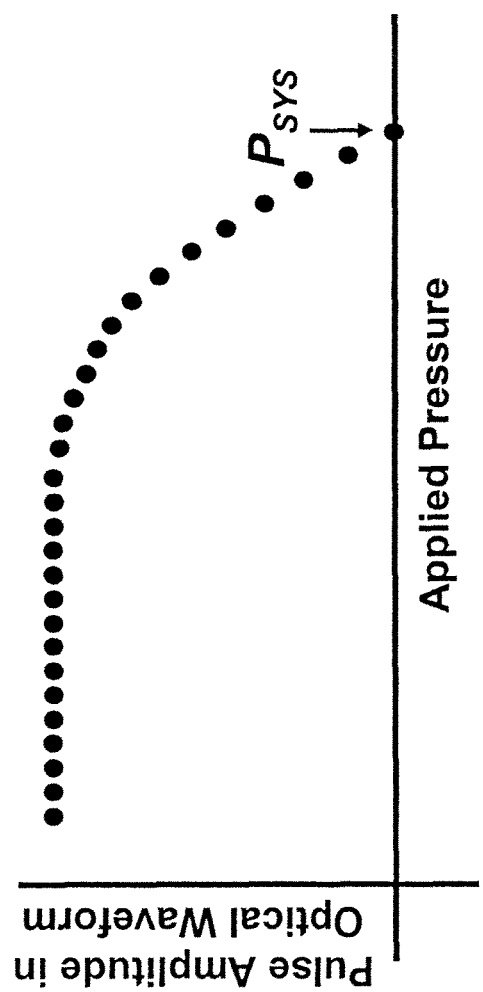

FIG. 3 shows, in more detail, graphs of the time-dependent pressure 121, optical 122, and electrical 123 waveforms measured during the pressure-dependent measurement. FIGS. 4A and 4B show, respectively, how PTT and the optical pulse amplitude determined from the optical 122 and electrical 123 waveforms vary with applied pressure for a typical patient. Pulses in the optical waveform 122 have no amplitude when the applied pressure is greater than systolic pressure (indicated by the dashed line 119) in the underlying artery. The pulses begin to appear when the applied pressure is equivalent to systolic blood pressure. Their amplitude increases, and their PTT decreases, as applied pressure decreases. These trends continue until diastolic pressure is reached. At this point, the amplitude of the pulses and the associated PTT values are relatively constant. QRS complexes in electrical waveform 123 are unaffected by the applied pressure.

During an actual pressure-dependent measurement, the body sensor collects data like that shown in FIGS. 4A and 4B, for an individual patient. A conventional peak-detecting algorithm running on the microprocessor in the body sensor detects the onset of the optical pulse amplitude, shown in FIG. 4B, to make a direct measurement of systolic blood pressure. Alternatively, a 'fitting' algorithm can model the systematic decrease in pulse amplitude with applied pressure to estimate systolic blood pressure. This involves fitting a mathematical function (e.g. a linear function) to the measurement data using well-known techniques.

Similarly, for a given patient, the microprocessor analyzes the variation between applied pressure and PTT, shown graphically in FIG. 4A, to estimate the relationship between blood pressure and PTT. As shown in Equation 1, below, this relationship is best described with a mathematical model that first estimates how the patient's 'effective' mean arterial blood pressure (MAP*(P)) varies with applied pressure ($P_{applied}$). The model assumes that pressure applied by the armband occludes the patient's brachial artery, and thus temporarily decreases blood flow. This, in turn, increases blood pressure directly underneath the armband, and reduces blood pressure in the downstream radial, ulnar, and finger arteries. The net effect is a temporary, pressure-dependent reduction in the patient's mean arterial blood pressure (MAP), indicated in equation 1 as $\Delta MAP(P)$, during the pressure-dependent measurement. An empirically determined factor (F) accounts for the ratio between the region of increased blood pressure (underneath the armband; approximately 10 cm) and the larger region of decreased blood pressure (the length of the arm downstream from the armband; approximately 50 cm). F is typically between 0.6 and 0.9, and is preprogrammed into the algorithm prior to measurement.

$$\Delta MAP(P)=F*(P_{applied}-DIA)$$

$$MAP*(P)=MAP-\Delta MAP(P) \quad (1)$$

Using Equation 1, paired values of PTT and MAP*(P) are determined for each heartbeat as the applied pressure increases from the diastolic pressure to mean arterial pressure. This approach yields multiple data points during a single pressure-dependent measurement that can then be fit with a mathematical function (e.g. a linear function) relating PTT to mean arterial pressure. Typically these parameters are inversely related, i.e. PTT gets shorter and blood pressure increases. In typical embodiments, therefore, an inverse linear relationship determined during the pressure-dependent measurement is then used during subsequent pressure-free measurements to convert the measured PTT into blood pressure values.

In Equation 1, the values for diastolic blood pressure (DIA) and mean arterial pressure (MAP) are determined with an oscillometric blood pressure measurement during inflation. Systolic blood pressure (SYS) can either be determined indirectly during the oscillometric blood pressure measurement, or directly using the above-described method involving the pulse amplitude in the optical waveform. From these values, the SYS/MAP and DIA/MAP ratios can be determined. These ratios are typically constant for a given patient over a range of blood pressures. They can be used during the pressure-free measurements, along with the PTT-dependent mean arterial pressure, to determine systolic and diastolic blood pressures.

The oscillometric blood pressure measurement analyzes the pressure waveform (121 in FIG. 3) that is measured by the armband. Performing this measurement during inflation expedites the measurement and increases patient comfort. In contrast, most conventional cuff-based systems using the oscillometric technique analyze their pressure waveform during deflation, resulting in a measurement that is roughly 4 times longer than the composite technique's pressure-dependent measurement. Inflation-based measurements are possible because of the composite technique's relatively slow inflation speed (typically 5-10 mmHg/second) and the high sensitivity of the pressure sensor used within the body sensor. Moreover, measurements made during inflation can be immediately terminated once systolic blood pressure is calculated. In contrast, conventional cuff-based measurements made during deflation typically apply a pressure that far exceeds the patient's systolic blood pressure; pressure within the cuff then slowly bleeds down below the diastolic pressure to complete the measurement.

FIGS. 5A and 5B show graphs of PTT as a function MAP*(P) (FIG. 5A) and MAP (FIG. 5B) for a single patient. Each data point 126, 129 in the graphs includes error bars representing an approximate measurement error. In FIG. 5A, the data points 126 are determined during a single, 30-second pressure-dependent measurement of the composite technique; each data point represents PTT and MAP*(P) values for an individual heartbeat. These data points are derived, for example, by combining measurements similar to those shown in FIG. 4A (PTT as a function of applied pressure) and Equation 1 (MAP*(P) calculated from applied pressure). In contrast, the two data points 129 in FIG. 5B are derived by simply measuring PTT and MAP during separate blood pressure measurements. Each measurement normally takes about 60 seconds to complete; they are ideally done at separate points in time when the patient's blood pressure (and corresponding PTT) differs by a measurable amount.

The two graphs illustrate the advantages of determining a patient-specific relationship between PTT and blood pressure during the composite technique's pressure-dependent measurement. As shown in FIG. 5A, the data points 126 vary over approximately a relatively large range in blood pressure (typically 15 mmHg or more); they are typically tightly correlated, and, despite any measurement error, can be easily fit with a single linear equation (y=Mx+B) shown by the dashed line 125. In contrast, if the patient's blood pressure is relatively stable, the two data points 129 of FIG. 5B can have similar values, even if they are measured several hours apart. These two values can yield fits with different linear equations ($y=M_1x+B_1$ and $y=M_2x+B_2$ and) even when the measurement error is low. Using an inaccurate linear equation in this instance can, in turn, result in an inaccurate relationship between PTT and blood pressure. Ultimately this adds error to the PTT-based blood pressure measurement.

Figure 6A:
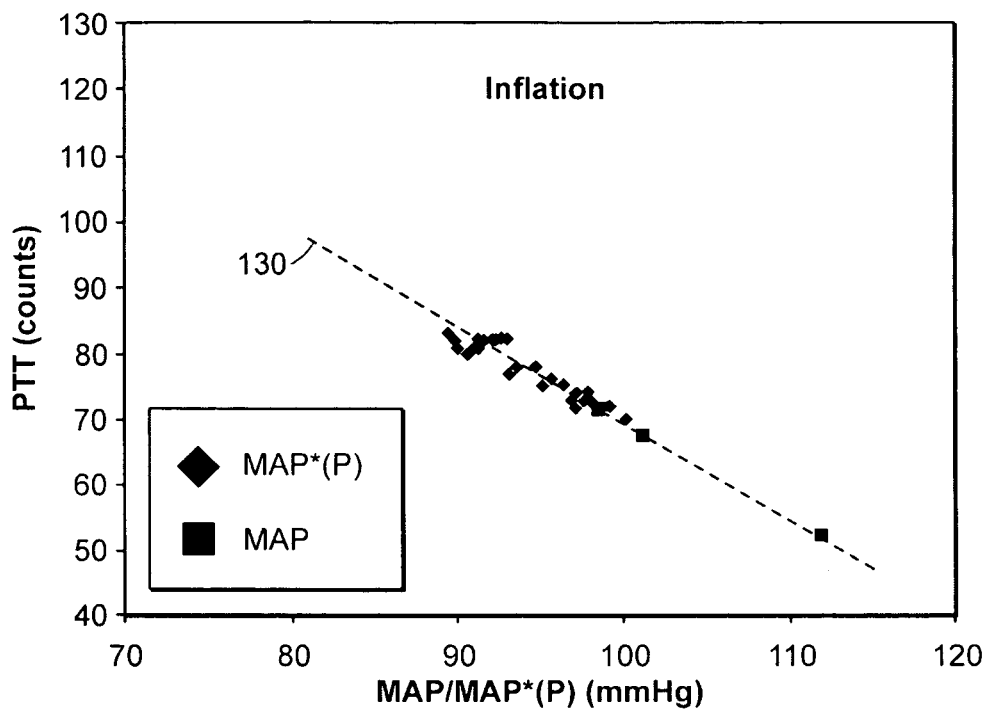
FIG. 6A shows a graph of PTT as a function of both MAP*(P) (measured during inflation using the pressure-dependent measurement of the composite technique) and MAP (measured for two separate blood pressure values) for a single patient.
Figure 6B:
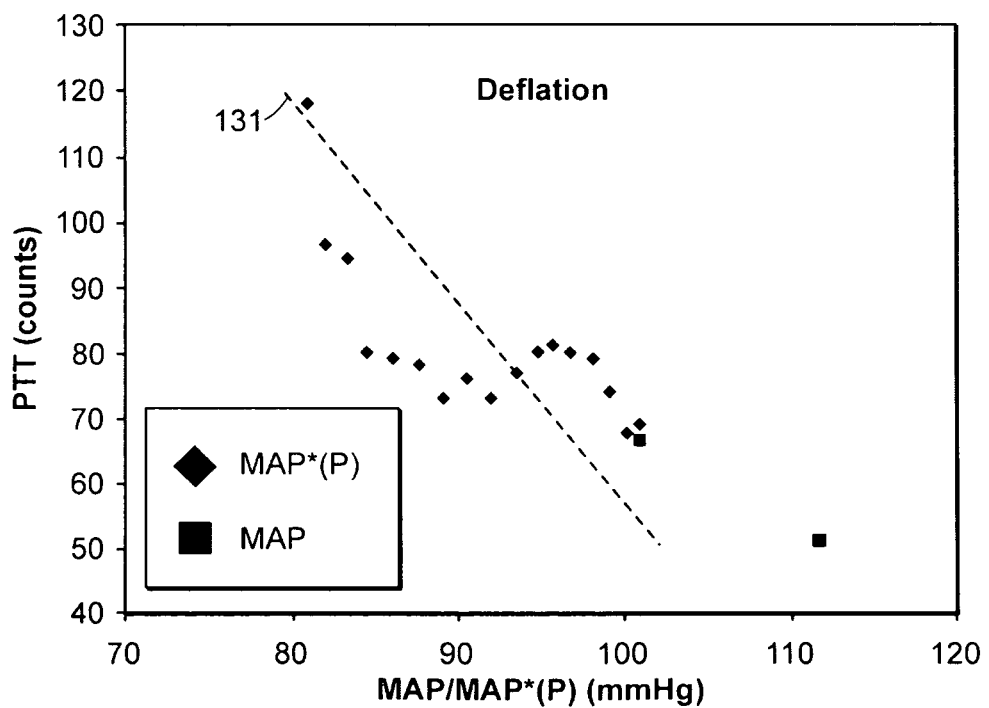
FIG. 6B shows a graph of PTT as a function of both MAP*(P) (measured during deflation using the pressure-dependent measurement of the composite technique) and MAP (measured for two separate blood pressure values) for a single patient.
Figure 7A:
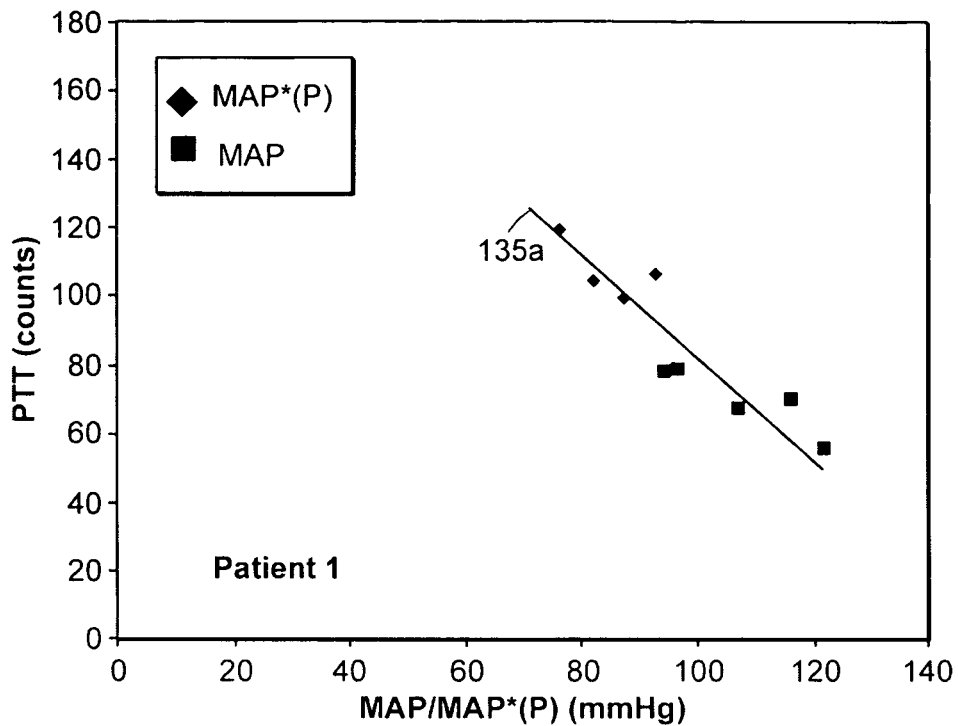
FIGS. 7A-7E show graphs of PTT as a function of both MAP*(P) (measured during inflation using the pressure-dependent measurement of the composite technique) and MAP (measured for two separate blood pressure values) for five unique patients.
Figure 7B:
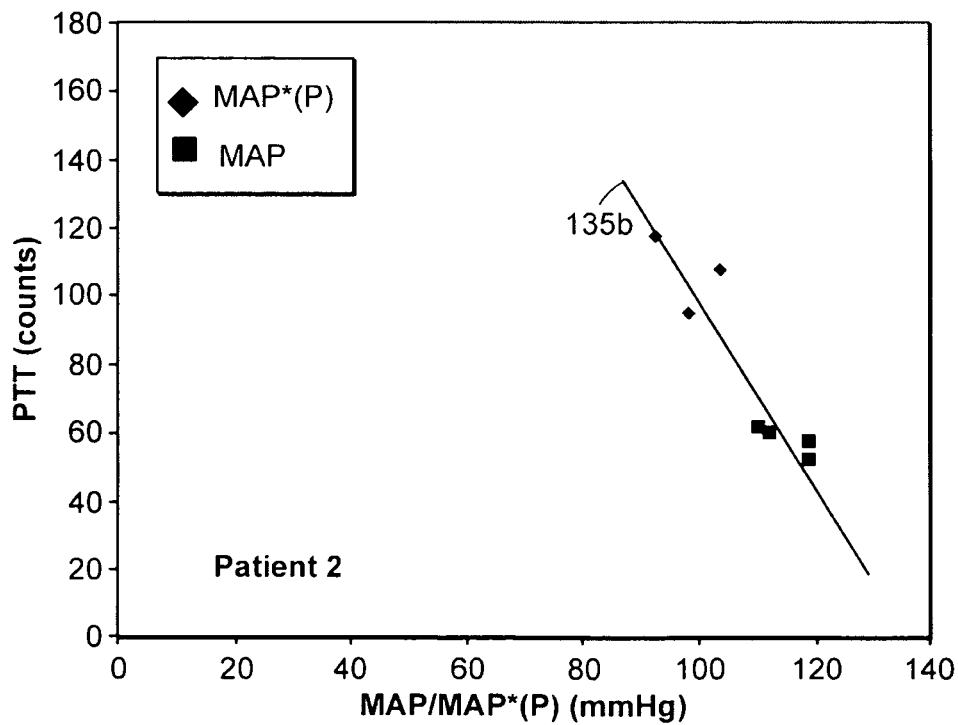
Figure 7C:
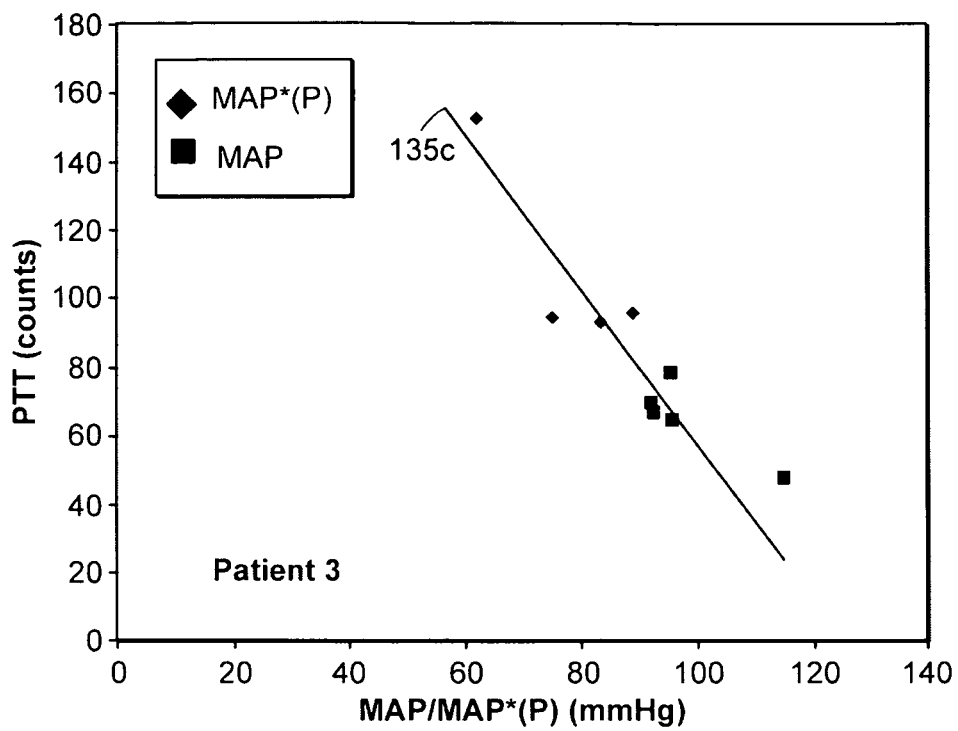
Figure 7D:
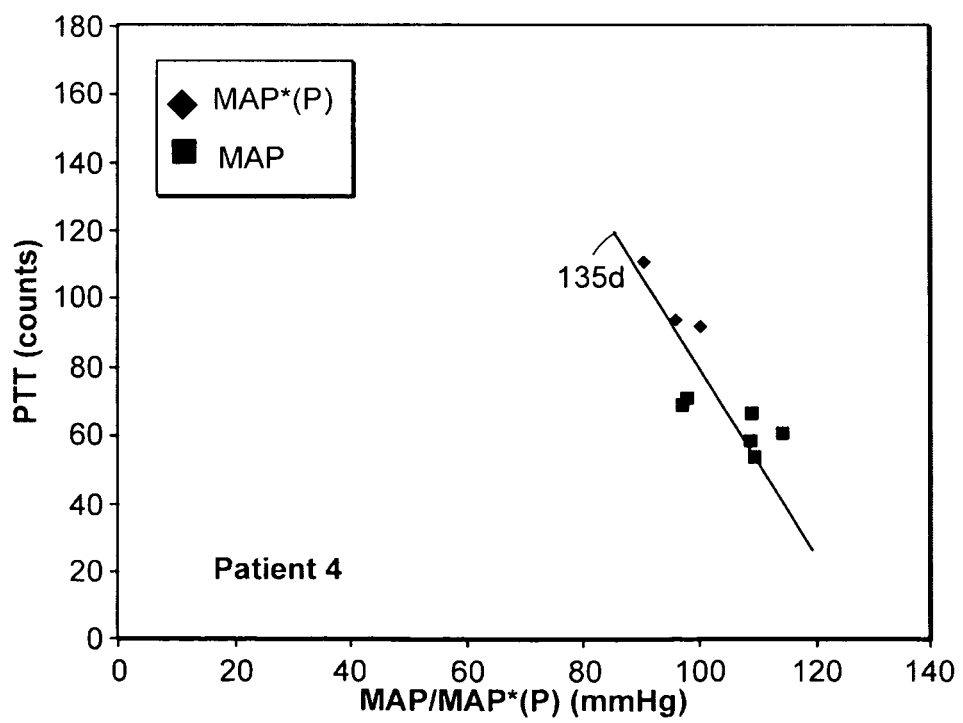
Figure 7E:
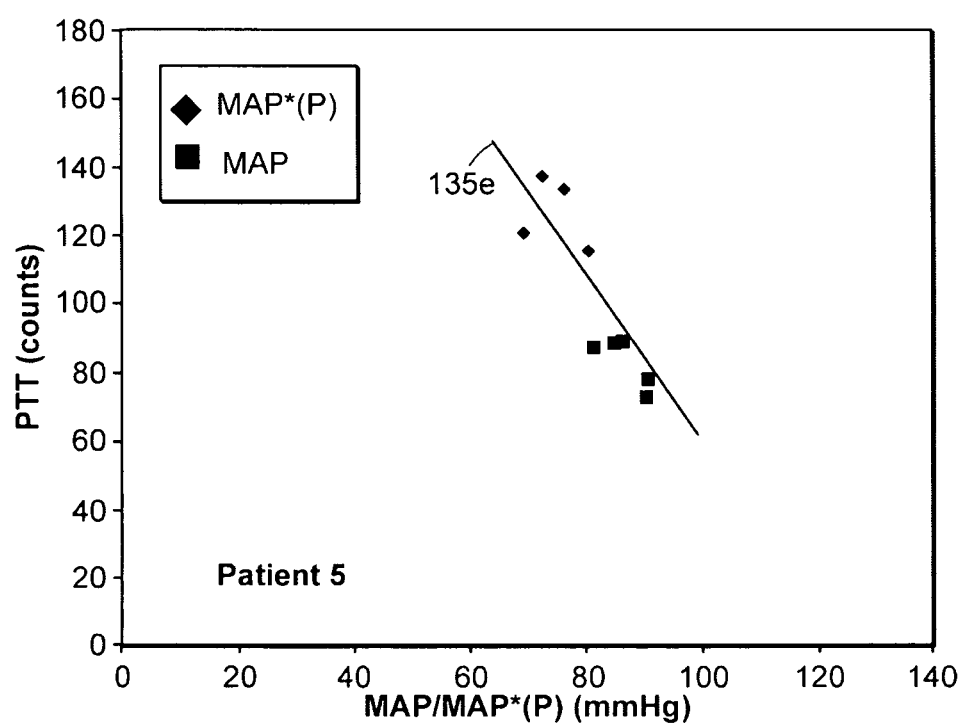

FIGS. 6A and 6B show actual PTT vs. MAP*(P) and MAP data, measured for a single patient, during a pressure-dependent measurement that uses inflation (FIG. 6A) and deflation (FIG. 6B). In the figures the triangles indicate PTT vs. MAP*(P) determined during the composite technique's pressure-dependent measurement. These data represent a calibration of the blood pressure measurement. The pink squares indicate subsequent, measurements wherein MAP is determined using an automated blood pressure cuff, and PTT is determined using the body sensor described herein. As is clear from the figures, the values of PTT vs. MAP*(P) measured during inflation (FIG. 6A) have a tight, well-correlated distribution compared to those measured during deflation (FIG. 6B). This indicates that a calibration determined from a pressure-dependent measurement made during inflation is likely more accurate than one made during deflation. Without being bound by any theory, this discrepancy may be due to an inflation-based pressure-dependent measurement that gradually reduces blood flow in an underlying artery until it is ultimately occluded. In contrast, a deflation-based measurement first fully occludes the artery, and then gradually reduces the occlusion as the armband deflates. Dammed-up blood rapidly flows through the artery during this process. This increase in blood flow may cause turbulence and other complicated hemodynamic events that add variability to the PTT value. Such processes are likely not present during an inflation-based measurement.

In FIG. 6A, a linear fit to the values of PTT vs. MAP*(P), shown by the dashed line 130, also fits the measurements of PTT vs. MAP. This indicates a calibration determined during the pressure-dependent measurement (triangles) can be used to accurately measure blood pressure values made during subsequent pressure-free measurements (squares). In FIG. 6B, the linear fit to the PTT vs. MAP*(P) values, shown by the dashed line 131, does not accurately fit the measurements of PTT vs. MAP. This result is expected based on the variability of the PTT vs. MAP*(P) values, and indicates that this calibration has a relatively low accuracy compared to that made during inflation.

FIGS. 7A-E is similar to FIG. 6A, and show data for 5 unique patients. The graphs show both calibration points of PTT vs. MAP*(P) values made during inflation-based pressure-dependent measurements (triangles), and subsequent values of MAP vs. PTT (squares). The MAP vs. PTT measurements were made with, respectively, an automated blood pressure device and the body sensor described herein. As is the case for FIG. 6A, the data indicate that the inflation-based calibration measurement accurately predicts the subsequent PTT-dependent blood pressure measurements. These data additionally show that this holds for a range of patients. The lines 135*a-e* in the graphs represent the best fits to the PTT vs. MAP*(P) values. As with FIG. 6A, these lines 135*a-e* also accurately fit the PTT vs. MAP data. The variation of the slope and y-intercept values for the different lines in the figures is likely due to patient-to-patient variation in arterial properties.

Figures 8A, 8B:
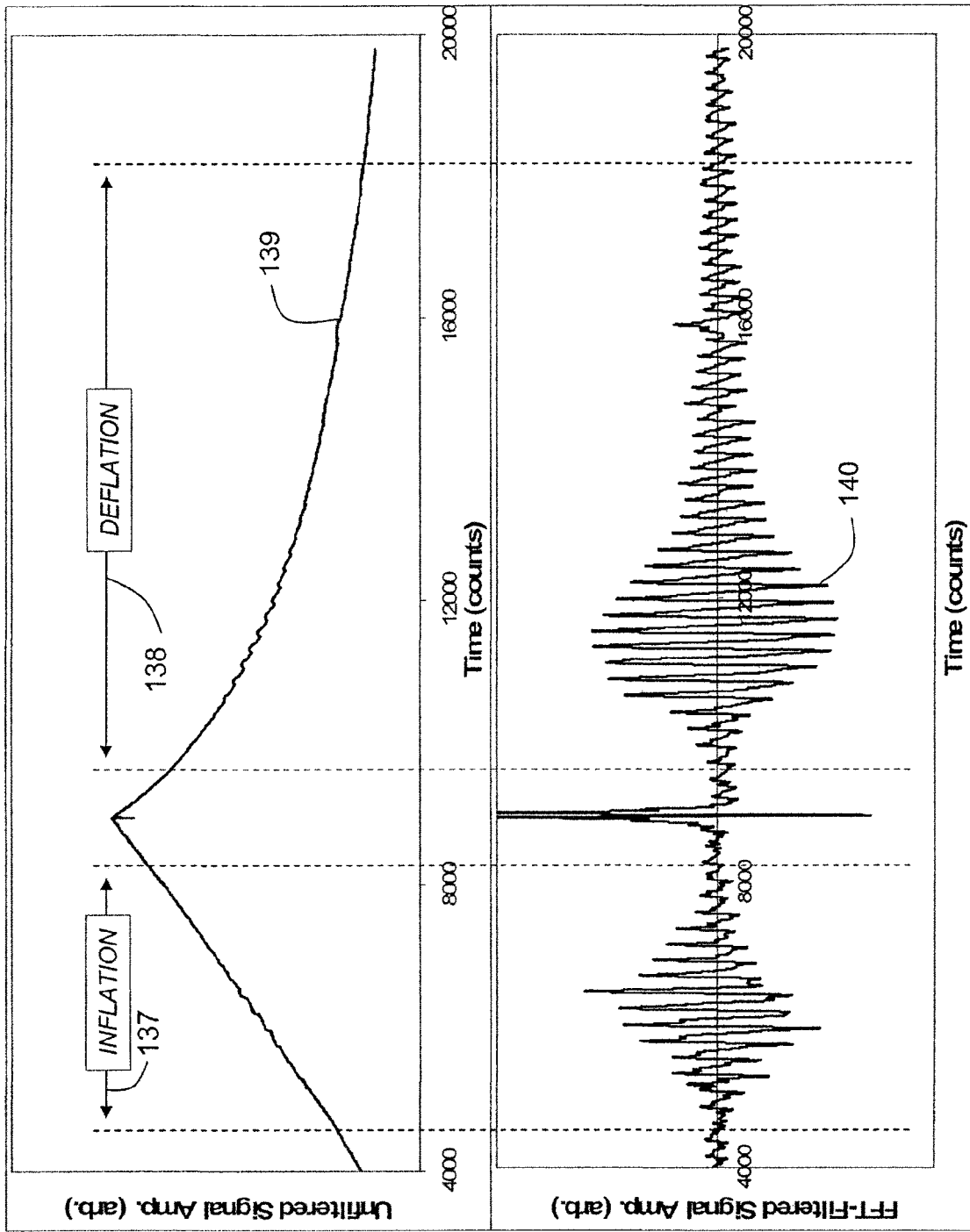
FIGS. 8A and 8B show graphs of, respectively, the time-dependent pressure waveform measured during both inflation and deflation, and the same waveform after being filtered with a digital bandpass filter based on Fourier transforms.

FIG. 8A illustrates the equivalency between inflation-based and deflation-based oscillometric blood pressure measurements. The top portion of the figure shows an unfiltered pressure waveform 139, measured during the pressure-dependent measurement, which includes periods of both inflation 137 and deflation 138. Pulses associated with the patient's heartbeat couple into a bladder in the armband during both periods. Following a measurement, the pressure waveform 139 is processed using a 0.5-5.0 Hz digital bandpass filter to remove the slowly varying baseline. As shown in FIG. 8B, filtering results in a time-dependent pressure waveform 140 featuring separate pulse trains measured during both inflation and deflation; the time-dependent amplitudes of each pulse in the train are characterized by a Gaussian envelope. Pressure corresponding to the peak of the Gaussian envelope represents a direct measurement of mean arterial pressure. Diastolic blood pressure, which is measured indirectly, corresponds to a pressure less than mean arterial pressure when the ratio of the envelope to its maximum value is 0.72. This ratio, along with the ratio for systolic blood pressure (typically 0.55), is described in more detail in U.S. Pat. No. 6,719,703, the contents of which are incorporated herein by reference.

Figure 9:
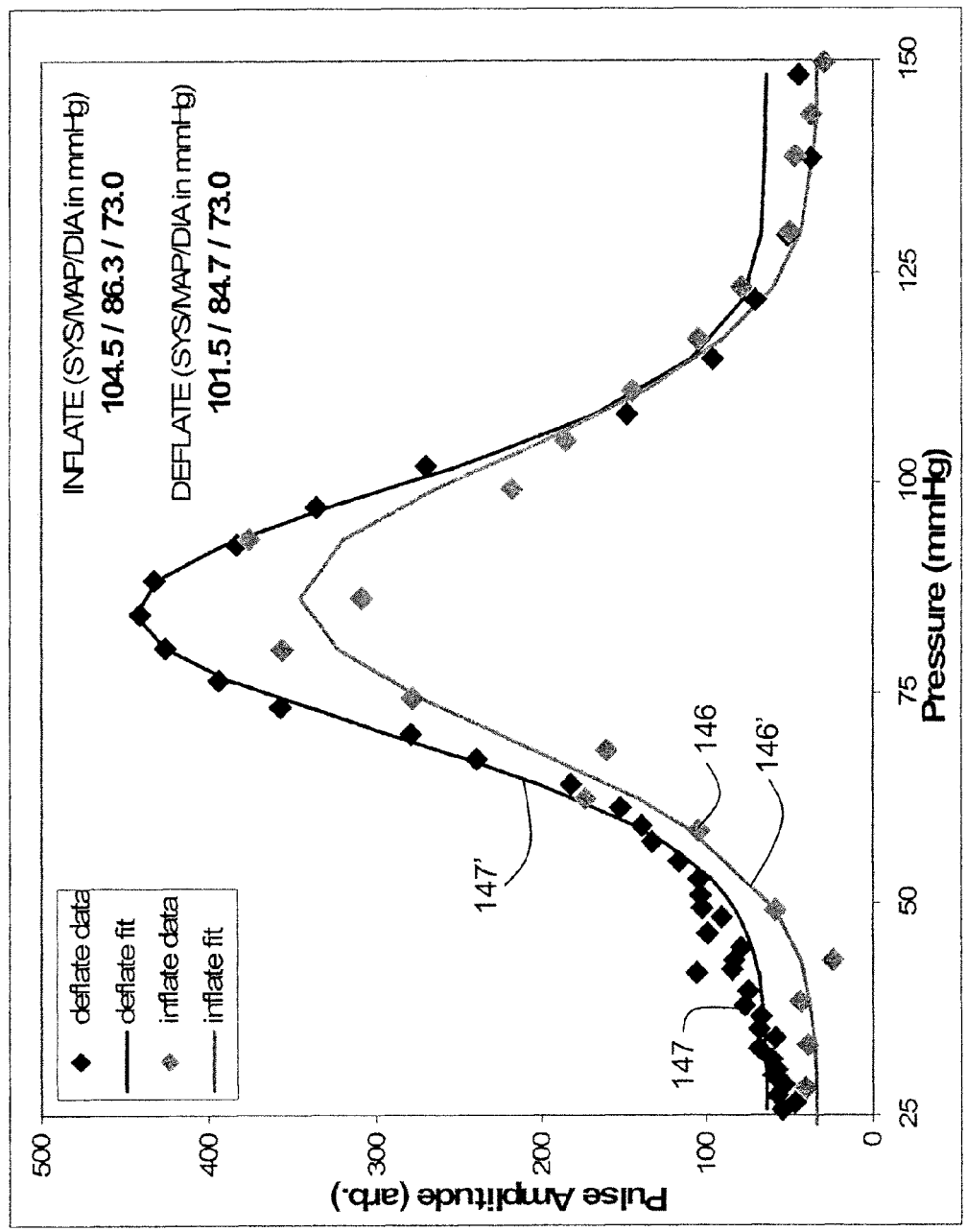
FIG. 9 shows a graph of the amplitude of pressure pulses measured from the graph of 9B as a function of pressure during both inflation and deflation.

FIG. 9, for example, shows a plot of pulse amplitude as a function of pressure generated using the filtered pressure waveform of FIGS. 8A and 8B. Data are shown for inflation 146 (gray data points and line) and deflation 147 (black data points and line). Both data 146, 147 are fit with a Gaussian function F(p), shown in the figure as solid lines 146', 147' and described in Equation 2 below, to accurately determine mean arterial pressure. The maximum pulse amplitude is best determined by calculating the maximum value of the Gaussian function 146', 147'. In Equation 2, the pressure corresponding to the maximum value of the Gaussian function is MAP. Systolic blood pressure can also be determined from the Gaussian function, and typically is the pressure above MAP that corresponds to an amplitude of 0.55 times the maximum amplitude. Although as described above, this represents an indirect measurement, and is thus not as accurate as that determined directly using the optical waveform.

$$F(P) = A\exp[-(P_{applied} - \text{MAP})^2/2\sigma^2] + B \quad (2)$$

In Equation 2, $P_{applied}$ is pressure, $\sigma$ is the full-width half-maximum of the Gaussian function, A is its amplitude, and B is a baseline value accounting for residual pressure. Analyzing the data in this way effectively increases the accuracy of the composite technique, as the fit draws a smooth, continuous line through data and thus partially accounts for any scatter caused, e.g., by patient motion. Erroneous data points can be removed to improve the accuracy of this technique. For example, data points that fall outside of the ideal fit by a pre-determined amount (e.g., 1 standard deviation) may be removed from the calculation. Blood pressure values determined from the fit are shown in the upper right-hand corner of the figure.

In an alternate embodiment, the filtered time-dependent pressure waveform 140 in FIG. 8B can be filtered again with a second digital low-pass filter (<2 Hz) to remove any high-frequency components associated with individual pulses in the waveform. This results in a smooth, continuous envelope with a Guassian-type shape (similar to the Gaussian functions 146', 147' in FIG. 9) that can be analyzed directly, as opposed to being fit, to determine blood pressure values.

Figure 10:
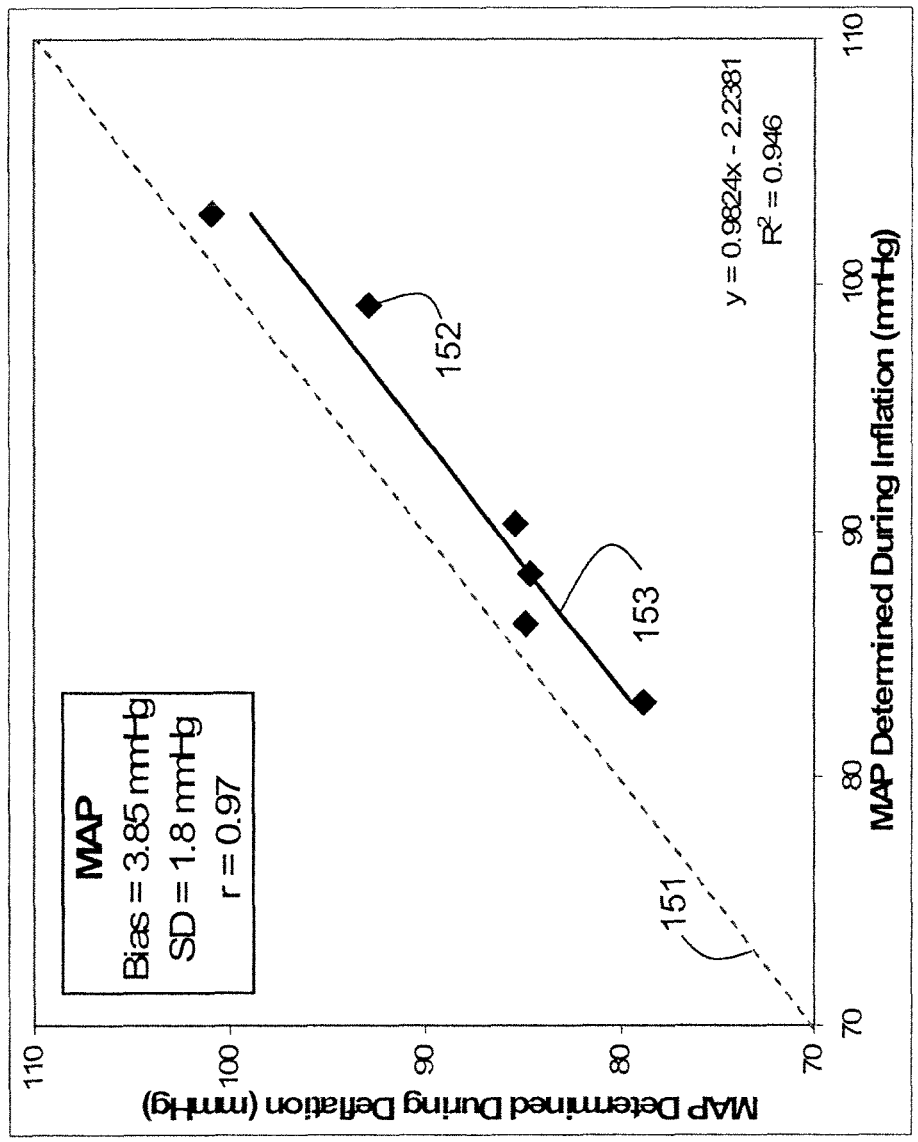
FIG. 10 shows a graph comparing mean arterial pressure measured during inflation and deflation.

Blood pressure values calculated during inflation and deflation are not necessarily equivalent. FIG. 10, for example, shows a graph of mean arterial pressure measured sequentially during inflation and deflation for six patients using the above-described technique. The graph includes a series of data points 152 which are fit with a linear function 153. As is clear from the graph, there is a well-defined bias between measurements made during inflation and deflation: mean arterial pressure measured during inflation has a value that is, on average, 3.85 mmHg higher than on deflation. Perfect correlation is shown in the graph by the dashed line 151. The experimentally determined bias, for example, could be due to artifacts introduced by conventional oscillometric blood pressure measurements made during deflation. In general, blood pressure values determined during inflation appear more representative of the patient's true blood pressure. Unlike measurements done during deflation, these measurements are not preceded by a potentially disruptive pressure that far exceeds the patient's systolic blood pressure, and which might introduce artifacts into the measurement.

Comparative measurements (for, e.g., FDA 510(k) clearance) using either the oscillometric or auscultatory techniques are almost always performed during deflation. Thus, to improve correlation between these measurements and the pressure-dependent measurement of the composite technique, a bias of approximately 4 mmHg may be added to the value of mean arterial pressure.

The pressure-dependent measurement of the composite technique determines systolic and mean arterial pressures directly, and diastolic pressure indirectly from both PTT and the pressure waveform. Diastolic pressure (DIA) can be determined with relatively high accuracy from the direct-determined systolic (SYS) and mean arterial pressures (MAP) by using a geometric mean, as shown in Equation 3 below:

$$(MAP)^2 = SYS*DIA$$

$$DIA=(MAP)^2/SYS \qquad (3)$$

Recent studies have shown that this approach is relatively accurate compared to conventional methods (see, e.g., Chemla D, Antony I, Zamani K, and Nitenberg A., Mean Aortic Pressure Is The Geometric Mean Of Systolic And Diastolic Aortic Pressure, *J Appl Physiol* 99: 2278-2284, 2005, the contents of which are incorporated herein by reference). In an alternative method, described in the same reference and shown below in Equation 4, the calculation for diastolic blood pressure takes into account the patient's heart rate to further improve its accuracy:

$$MAP=DIA+[0.33+(HR*0.0012)]*(SYS-DIA)$$

$$a=[0.33+(HR*0.0012)]$$

$$DIA=(MAP-a*SYS)/(1-a) \qquad (4)$$

As described above, with reference to Equation 1, PTT and mean arterial blood pressure are typically related in an inverse, linear equation. This equation, along with ratios that relate mean pressure to both systolic and diastolic pressures, are determined during the initial pressure-dependent measurement. In an alternate embodiment, the body sensor initially calculates blood pressure using separate pre-determined linear relationships, shown below in Equations 5 and 6. The y-intercepts ($B_{sys}$, $B_{dia}$) of the linear relationships are equal to the initial values of, respectively, systolic and diastolic blood pressure determined from the pressure-dependent measurement. The initial slope ($M_{sys}$, $M_{dia}$) values shown below are determined by analyzing data from nearly 100 patients using the MIT/Harvard MIMIC database (see, e.g., www.physionet.org and 'Zong W, Moody G B, and Mark R., Effects of vasoactive drugs on the relationship between ECG-pulse wave delay time and arterial blood pressure in ICU patients. *Computers in Cardiology* 25: 673-676, 1998', the contents of which are incorporated herein by reference). The initial values of these parameters are as follows:

$$M_{sys}=-4.80 \text{ mmHg/ms}$$

$$M_{dia}=-2.56 \text{ mmHg/ms} \qquad (5)$$

As the pressure-free measurement progresses, software in the body sensor analyzes PTT values and initiates a second pressure-dependent measurement once PTT changes by, e.g., +/−10%. Software compares PTT and blood pressures values from this second measurement to values from the initial measurement to calculate patient-specific values of ($M_{sys}$, $M_{dia}$) and ($B_{sys}$, $B_{dia}$). These values are then used going forward for either 4 hours or if PTT changes again by, e.g., +/−10%. At this point, the patient-specific values of ($M_{sys}$, $M_{dia}$) and ($B_{sys}$, $B_{dia}$) are recalculated and used again.

$$SYS=(1/PTT)*(M_{sys})+(B_{sys})$$

$$DIA=(1/PTT)*(M_{dia})+(B_{dia}) \qquad (6)$$

In still other embodiments, combinations of the values from the Harvard/MIMIC database and the patient-specific parameters determined during the pressure-dependent measurement can be used to calibrate the body sensor.

The composite technique also includes an intermediate pressure-dependent measurement that determines systolic, diastolic, and means arterial pressures using an abbreviated applied pressure. In this case, to find systolic blood pressure, the algorithm can detect the amplitude of each pulse in the optical waveform, and fit them to a variety of mathematical models to 'predict' and extrapolate exactly where the amplitude decreases to zero. For example, the algorithm can fit the last eight data points in FIG. 4B to a linear function. In this case knowledge of the patient's heart rate (e.g. frequency and rhythmicity), as determined from the electrical waveform, can enhance the accuracy of the prediction and provide a confidence indicator of the metric. The algorithm may take a mathematical derivative of the optical waveform to eliminate any affects of the waveform's baseline. The above-described algorithms may then be used to predict disappearance of the pulse and thus the onset of systolic blood pressure.

During the intermediate pressure-dependent measurement, pressure is typically applied until just after mean arterial pressure is calculated as described above, and then terminated. At this point, the amplitude of the optical waveform is typically in decline, and can be fit with the linear function to predict systolic blood pressure. Both systolic and mean arterial pressures are then used to determine diastolic pressure, as described above. The intermediate pressure-dependent measurement is typically performed, for example, every 4 hours in place of the regular pressure-dependent measurement.

Figure 11:
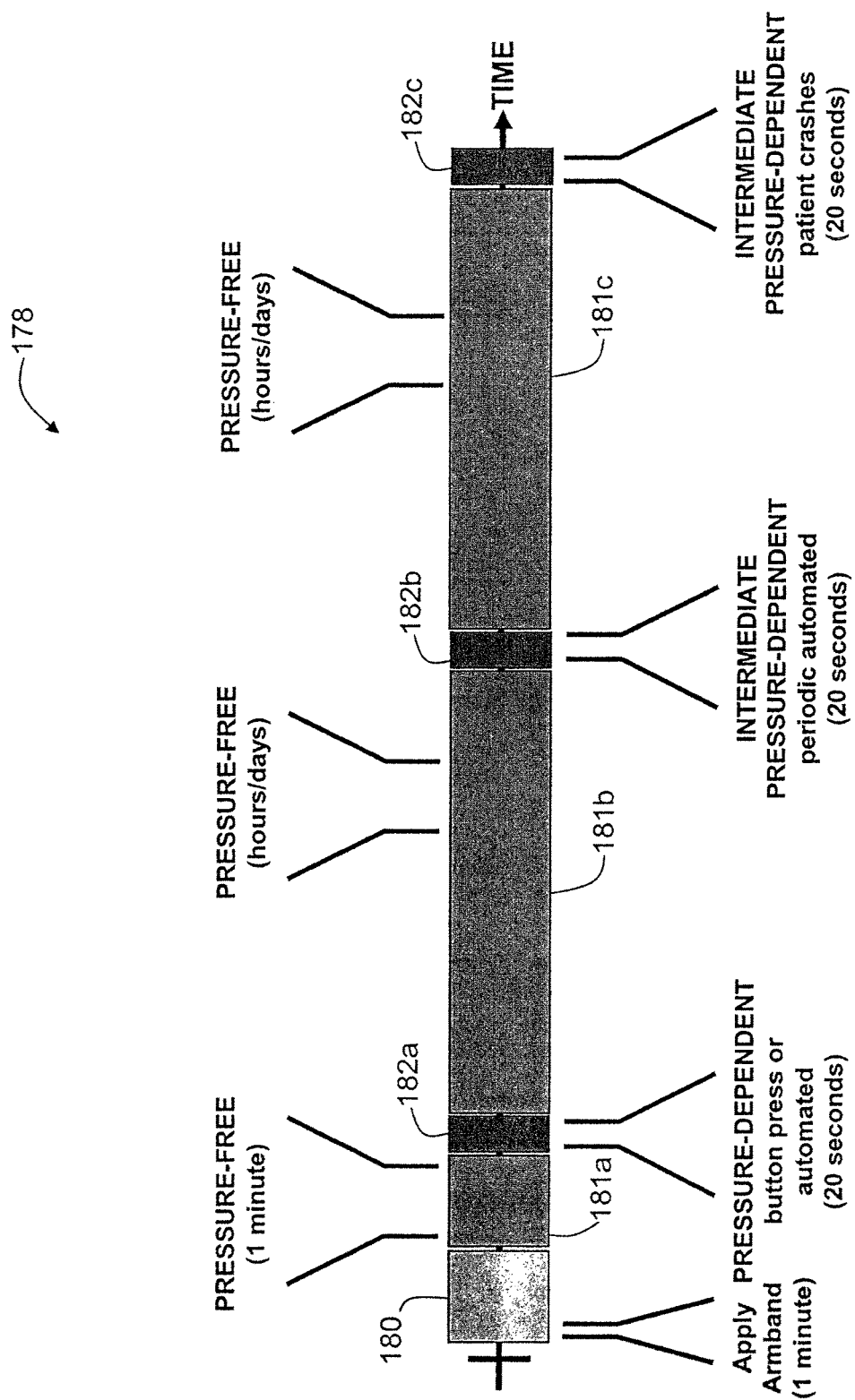
FIG. 11 is a schematic drawing showing a sequence of pressure-dependent and pressure-free measurements made during the composite technique.

FIG. 11 shows one possible sequence 178 of the composite technique's pressure-dependent (steps 182a), pressure-free (steps 181a, 181b, 181c), and intermediate pressure-dependent (steps 182b, 182c) measurements for a patient undergoing an extended hospital stay. During the stay, a medical professional applies the body sensor, optical sensor, and chest electrodes to the patient (step 180). This takes about 1 minute. The medical professional may also collect biometric information from the patient, such as their age, weight, height, gender, ethnicity, and whether they are on blood pressure medications, and enter these into the monitor using a graphical user interface and touchpanel. This information is then communicated wirelessly to the body sensor. Going forward, a microprocessor within the body sensor's electronics module first initiates a pressure-free measurement (step 181a) for about 1 minute, wherein the body sensor collects optical and electrical waveforms from the patient, determines their heart rate and PTT, and estimates their blood pressure. In the absence of an absolute blood pressure measurement from the composite technique's pressure-dependent measurement, the microprocessor may use PTT and the patient's biometric information to estimate blood pressure, as is described in the following co-pending patent applications: DEVICE AND METHOD FOR DETERMINING BLOOD PRESSURE USING 'HYBRID' PULSE TRANSIT TIME MEASUREMENT (U.S. Ser. No. 60/943,464; filed Jun. 12, 2007); and, VITAL SIGN MONITOR FOR CUFFLESSLY MEASURING BLOOD PRESSURE USING A PULSE TRANSIT TIME CORRECTED FOR VASCULAR INDEX (U.S. Ser. No. 60/943,523; filed Jun. 12, 2007). This process typically determines systolic and diastolic blood pressure with an accuracy of about ±10-15 mmHg.

The initial, approximate value for the patient's blood pressure and heart rate determined during the first pressure-free measurement (step 181a) can then be used to set certain parameters during the following first pressure-dependent measurement (step 182a). Knowledge of these parameters may ultimately increase the accuracy of the first pressure-dependent measurement (step 182a). Such parameters, for example, may include inflation time and rate, fitting parameters for determining the time-dependent increase in PTT and the time-dependent decrease in optical waveform amplitude during the pressure-dependent measurement. Of particular importance is an accurate value of the patient's heart rate determined during the first pressure-free measurement (step 181a). Since both PTT and amplitude can only be measured from a pulse induced by a heart beat, the algorithm can process heart rate and use it in the fitting process to accurately determine the pressure at which the optical waveform amplitude crosses zero.

Using parameters such as heart rate and initial estimated blood pressure, the first pressure-dependent measurement (step 182a) determines a relationship between PTT and blood pressure as described above with reference to Equations 1-5 above. This takes about 20 seconds. This measurement may occur automatically (e.g., after about 1 minute), or may be driven by the medical professional (e.g., through a button press). The microprocessor then uses this relationship and a measured value of PTT to determine blood pressure during the following pressure-free measurement (step 181b). This measurement step typically proceeds for a well-defined period of time (e.g., 4 hours), during which it continuously determines blood pressure. Typically, to conserve battery life, the body sensor averages PTT values over a 10-20 second period, and makes one blood pressure measurement every 3-5 minutes.

The microprocessor may also perform a pre-programmed or automated intermediate pressure-dependent measurement (step 182b) to correct any drift in the blood pressure measurement. As described above, this step involves only partial inflation of the bladder within the armband, during which the microprocessor fits the pressure-dependent decrease in the amplitude of pulses in the optical waveform to a linear model. This measurement takes less time than the first pressure-dependent measurement (step 182a), and accurately determines blood pressure values that are used going forward in a second pressure-free measurement (step 181c). As before, this measurement typically continues for a well-defined period of time. At some later time, if the patient experiences a sudden change in other vital signs (e.g., respiratory rate, heart rate, body temperature), the microprocessor may analyze this condition and initiate another pressure-dependent blood pressure measurement (step 182c) to most accurately determine the patient's blood pressure.

Figure 12:
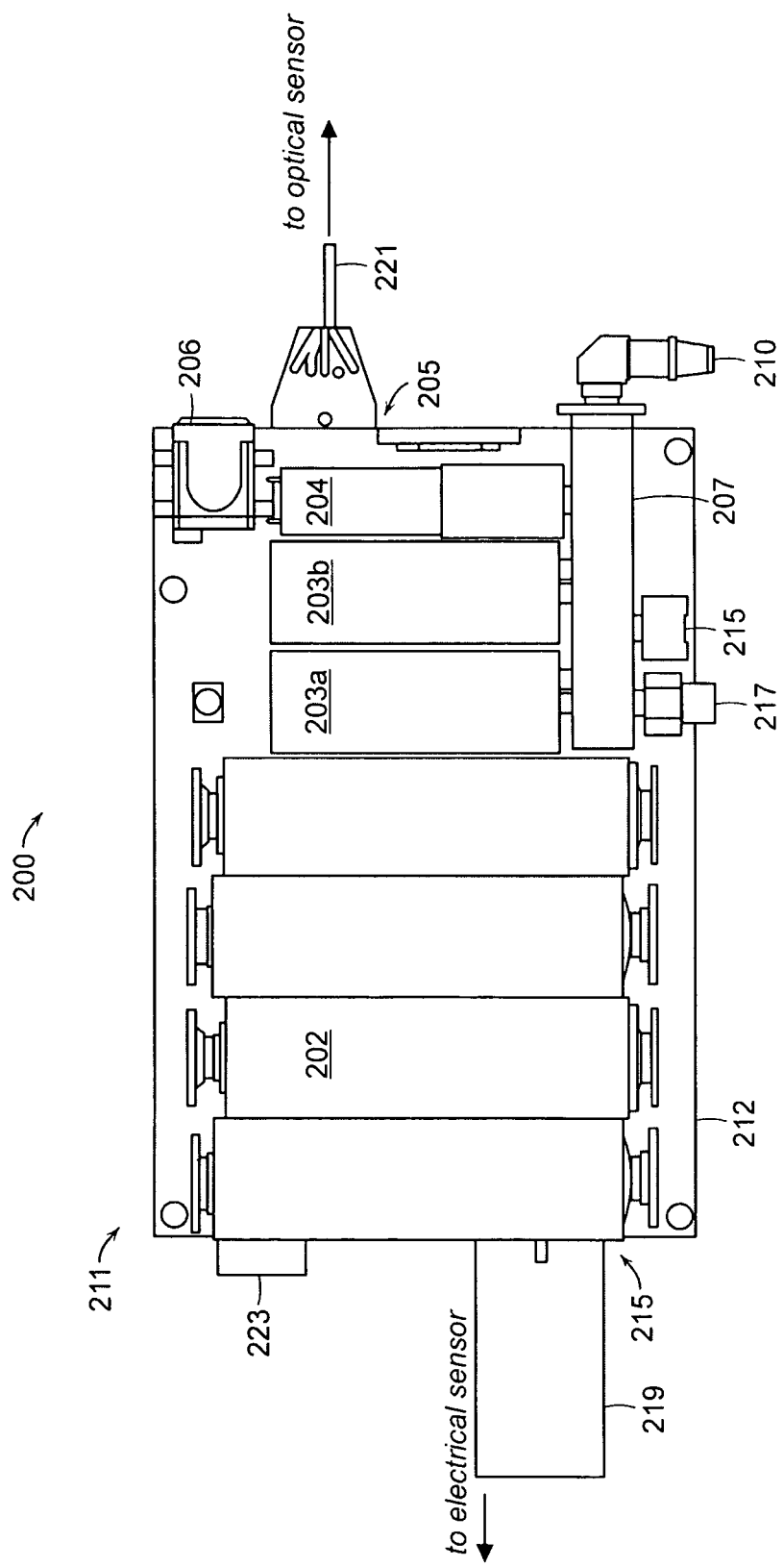
FIG. 12 is a top view of a circuit board used in the body sensor.

FIG. 12 shows a top view of the body sensor 200 used to conduct the above-described measurements. The body sensor 200 features a single circuit board 212 including connectors 215, 205 that connect through separate cables 219, 221 to, respectively, the electrical sensor (electrodes worn on the patient's chest) and optical sensor (worn on the patient's wrist). During both pressure-dependent and pressure-free measurements, these sensors measure electrical and optical signals that pass through the connectors 205, 215 to discrete circuit components 211 on the bottom side of the circuit board 212. The discrete components 211 include: i) analog circuitry for amplifying and filtering the time-dependent optical and electrical waveforms; ii) an analog-to-digital converter for converting the time-dependent analog signals into digital waveforms; and iii) a microprocessor for processing the digital waveforms to determine blood pressure according to the composite technique, along with other vital signs.

To measure the pressure waveform during a pressure-dependent measurement, the circuit board 212 additionally includes a small mechanical pump 204 for inflating the bladder within the armband, and first and second solenoid values 203a, 203b for controlling the bladder's inflation and deflation rates. The pump 204 and solenoid valves 203a, 203b connect through a manifold 207 to a connector 210 that attaches through a tube (not shown in the figure) to the bladder in the armband, and additionally to a digital pressure sensor 215 that senses the pressure in the bladder. The first solenoid valve 203a couples through the manifold 207 to a small 'bleeder' valve 217 featuring a small hole that slowly releases pressure. The second solenoid valve 203b is coupled through the manifold 207 and rapidly releases pressure. Typically both solenoid valves 203a, 203b are closed as the pump 204 inflates the bladder. For measurements conducted during inflation, pulsations caused by the patient's heartbeats couple into the bladder as it inflates, and are mapped onto the pressure waveform. The digital pressure sensor 215 generates an analog pressure waveform, which is then digitized with the analog-to-digital converter described above. The microprocessor processes the digitized pressure, optical, and electrical waveforms to determine systolic, mean arterial, and diastolic blood pressures. Once these measurements are complete, the microprocessor immediately opens the second solenoid valve 203b, causing the bladder to rapidly deflate.

Alternatively, for measurements done on deflation, the pump 204 inflates the bladder to a pre-programmed pressure above the patient's systolic pressure. Once this pressure is reached, the microprocessor opens the first solenoid valve 203a, which couples to the 'bleeder' valve 217 to slowly release the pressure. During this deflation period, pulsations caused by the patient's heartbeat are coupled into the bladder and are mapped onto the pressure waveform, which is then measured by the digital pressure sensor. Once the microprocessor determines systolic, mean arterial, and diastolic blood pressure, it opens the second solenoid valve 203b to rapidly evacuate the pressure.

Four AA batteries 202 mount directly on the circuit board 212 to power all the above-mentioned circuit components. The board 212 additionally includes a plug 206 which accepts power from a wall-mounted AC adaptor. The AC adaptor is used, for example, when measurements are made over an extended period of time. A rugged plastic housing (not shown in the figure) covers the circuit board 212 and all its components. A Bluetooth transmitter 223 is mounted directly on the circuit board 212 and, following a measurement, wirelessly transmits information to an external monitor.

Figure 13:
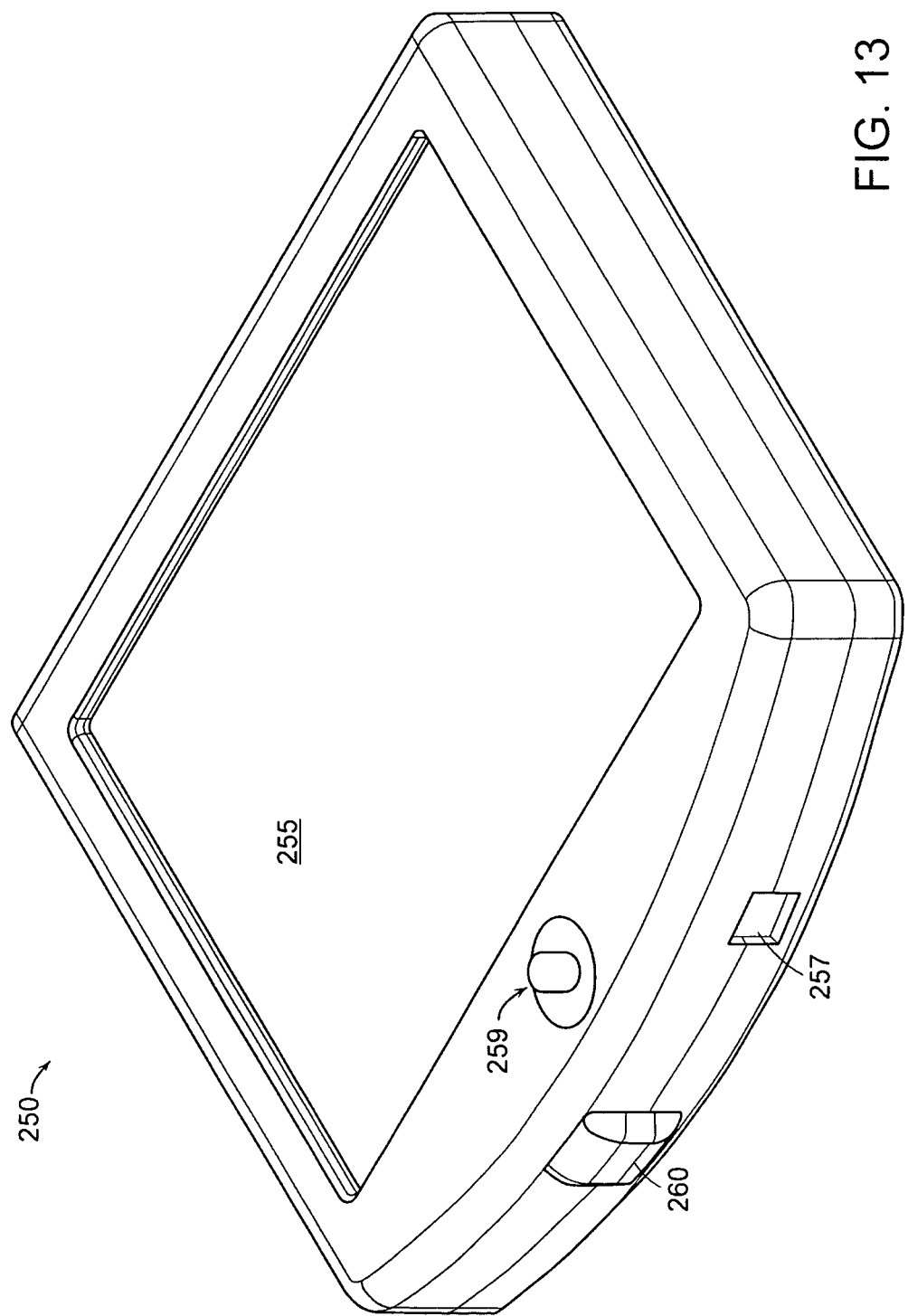
FIG. 13 is a three-dimensional plan view of the monitor.

FIG. 13 shows a three-dimensional plan view of the monitor 250 that receives the Bluetooth-transmitted information. The front face of the monitor 250 includes a touchpanel display 255 that renders an icon-driven graphical user interface, and a circular on/off button 259. During an actual measurement, the touchpanel display 255 renders vital sign information from the body sensor. Such a monitor has been described previously in BLOOD PRESSURE MONITOR (U.S. Ser. No. 11/530,076; filed Sep. 8, 2006) and MONITOR FOR MEASURING VITAL SIGNS AND RENDERING VIDEO IMAGES (U.S. Ser. No. 11/682,177; filed Mar. 5, 2007), the contents of which are incorporated herein by reference. The monitor 250 includes an internal Bluetooth transmitter (not shown in the figure) that can include an antenna 260 to increase the strength of the received signal. To pair with a body sensor, such as that shown in FIG. 9, the monitor 250 includes a barcode scanner 257 on its top surface. During operation, a user holds the monitor 250 in one hand, and points the barcode scanner 257 at a printed barcode adhered to the plastic cover surrounding the body sensor. The user then taps an icon on the touchpanel display 255, causing the barcode scanner 257 to scan the barcode. The printed barcode includes information on the body sensor's Bluetooth transceiver that allows it to pair with the monitor's Bluetooth transceiver. The scanning process decodes the barcode and translates its information to a microprocessor within the monitor 250. Once the information is received, software running on the microprocessor analyzes it to complete the pairing. This methodology forces the user to bring the monitor into close proximity to the body sensor, thereby reducing the chance that vital sign information from another body sensor is erroneously received and displayed.

Figure 14:
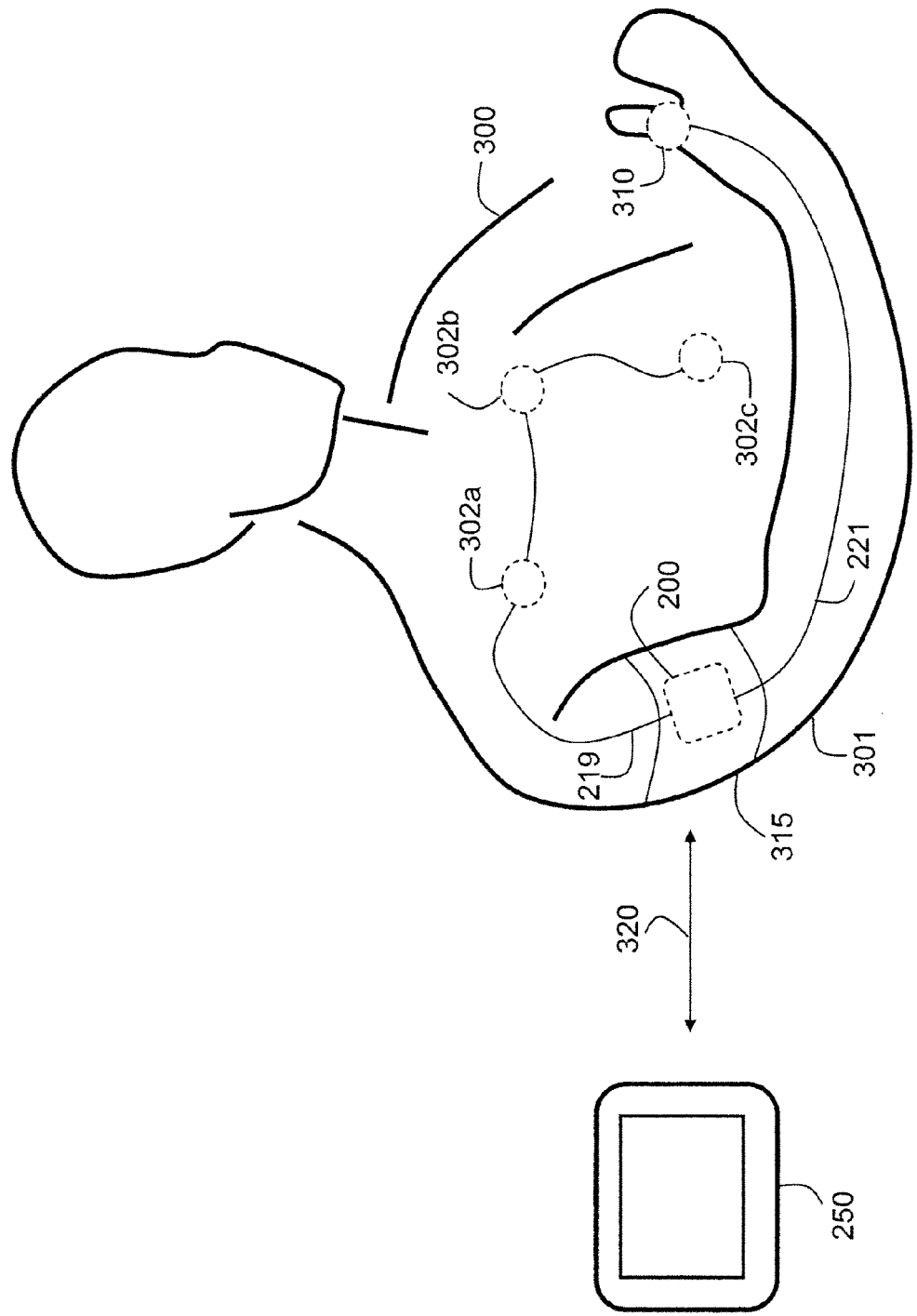
FIG. 14 is a schematic drawing of a patient wearing the body sensor of FIG. 12, which is in communication with the monitor of FIG. 13.

FIG. 14 shows a patient 300 wearing a body sensor 200, which communicates wirelessly (as shown by the arrow 320) with a remote monitor 250. The body sensor 200 attaches to the patient's arm 301 with an armband 315. Three disposable ECG electrodes 302a-c adhere to the patient's chest in a standard Einthoven's triangle configuration, and connect to the body sensor 200 though a first cable 219. These sensors 302a-c, in combination with the body sensor 200, measure an electrical waveform similar to that indicated by components 112a, 112b in FIG. 2, and 123 in FIG. 3. An optical sensor 310 wraps around the base of the patient's thumb with an adhesive band, and in combination with the body sensor 200 measures an optical waveform similar to that indicated by components 113a, 113b in FIG. 2, and 122 in FIG. 3. During a pressure-dependent measurement, pneumatic components (i.e. a pump, valves, and pressure manifold) within the body sensor 200 inflate a bladder within the armband 315, causing it to apply pressure to the patient's arm 301. As described above, the applied pressure has essentially no affect on the electrical waveform, but decreases the amplitude and delays the onset of pulses in the optical waveform. A microprocessor in the body sensor 200 processes waveforms measured during the pressure-dependent measurement to 'calibrate' the measure for the particular patient 300. Subsequent pressure-free measurements use the calibration, along with a PTT determined from the optical and electrical waveforms, to continuously determine the patient's blood pressure.

Figure 15:
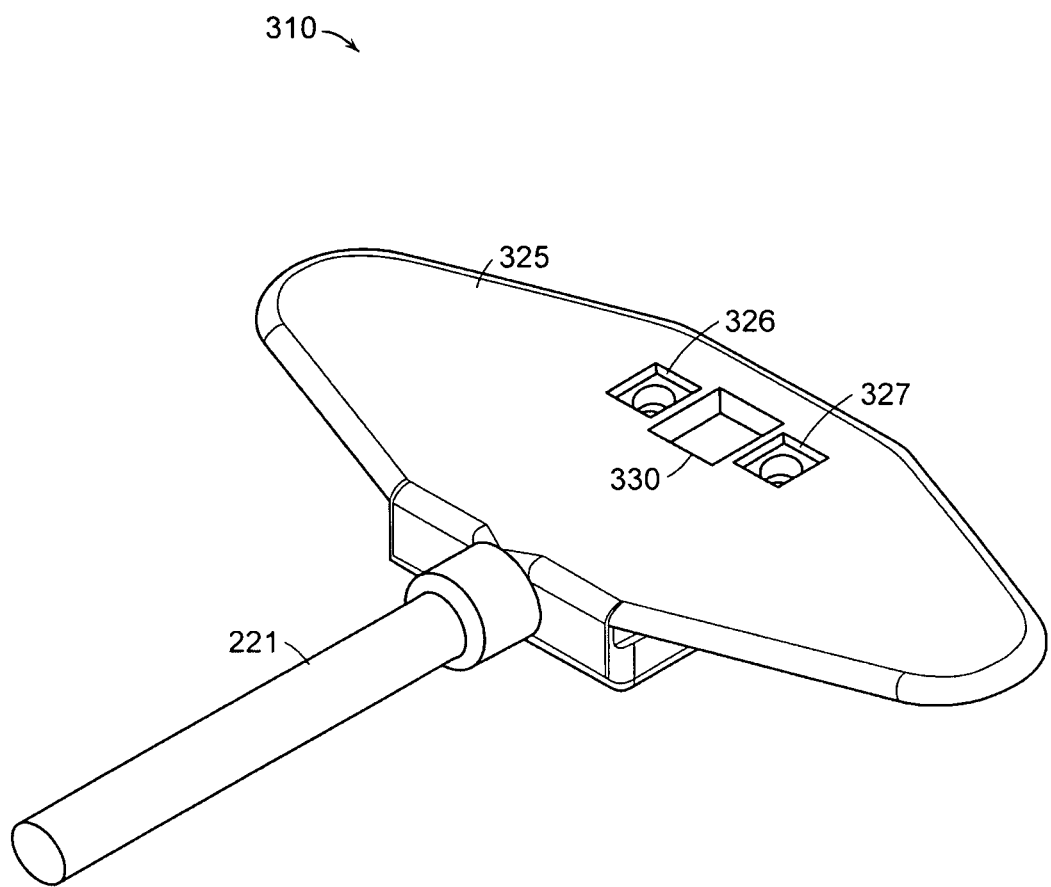
FIG. 15 is a three-dimensional plan view of an optical sensor that connects to the body sensor of FIG. 12 and measures an optical waveform similar to that shown in FIGS. 2 and 3.

FIG. 15 shows the above-described optical sensor 310, which adheres to the patient's thumb or the palm near the base of the thumb with an adhesive wrap and connects to the body sensor through a cable 221. The optical sensor 310 measures an optical waveform from the patient during both pressure-dependent and pressure-free measurements. In the embodiment shown in the figure, the optical sensor includes a single photodetector 330 surrounded by a pair of LEDs 326, 327, both operating near 570 nm. A flexible rubber backing 325 supports these optical components to make a measurement using a reflection-mode geometry. As described above, the optical components can be disposed in other configurations, e.g. the optical sensor 310 can include even more LEDs and photodetectors, or one or more separate optical modules, each including a single LED, photodetector, and analog amplifier. In still other embodiments, the LEDs and photodetector are disposed on opposite sides of the flexible rubber backing 325 so that they operate in a transmission-mode geometry when the backing is wrapped around the patient's thumb.

FIGS. 16A, 16B, 17A, 17B, 18A, 18B, 19A, 19B show data from a formal feasibility study conducted with the above-described composite technique. The study was conducted at a dialysis center located in San Diego, Calif., and monitored the accuracy of the composite technique for both one-time and continuous measurements from patients with end-stage renal disease during dialysis therapies typically lasting 3-4 hours. These patients provides a particularly challenging demographic for the composite technique, as they tend to have stiff, inelastic arteries that often make it difficult to accurately perform even conventional blood pressure measurements. For the study, blood pressure was measured during eight separate dialysis sessions conducted on five unique patients. A specialized blood pressure cuff, allowing simultaneous measurements using the composite, oscillometric (i.e. automated), and auscultatory (i.e. manual) techniques, was used during the studies. Measurements were made from the right arm of all but one patient, and both systolic and diastolic blood pressures were characterized. During dialysis, blood pressure was measured with the composite technique's pressure-free measurement every 40 seconds over the 3-4 hour dialysis period. Using the specialized cuff, every 15 minutes both pressure-dependent and pressure-free measurements were made with the composite technique, along with simultaneous measurements made using the oscillometric and auscultatory techniques. Both the pressure-dependent and pressure-free measurements made every 15 minutes were compared to those made by the oscillometric and auscultatory techniques to determine correlation. In addition, trends in the pressure-free measurements were compared to measurements made by the auscultatory technique to determine how well they predicted time-dependent blood pressure variations.

FIGS. 19A and 19B show time-dependent blood pressure measurements made during the study. The gray diamonds shown in each graph indicate pressure-free measurements made every 40 seconds; the black squares indicate auscultatory measurements made approximately every 15 minutes using the specialized cuff. Good correlation between the different measurements indicates the accuracy of the composite technique during dialysis. Perhaps more importantly, the composite measurements are made with relatively high frequency, and are thus more sensitive to short-term fluctuations in blood pressure that often occur during dialysis. The data shown in FIG. 19B, in particular, show well-defined, time-dependent oscillations in blood pressure, presumably instigated by the dialysis therapy.

Figure 16B:
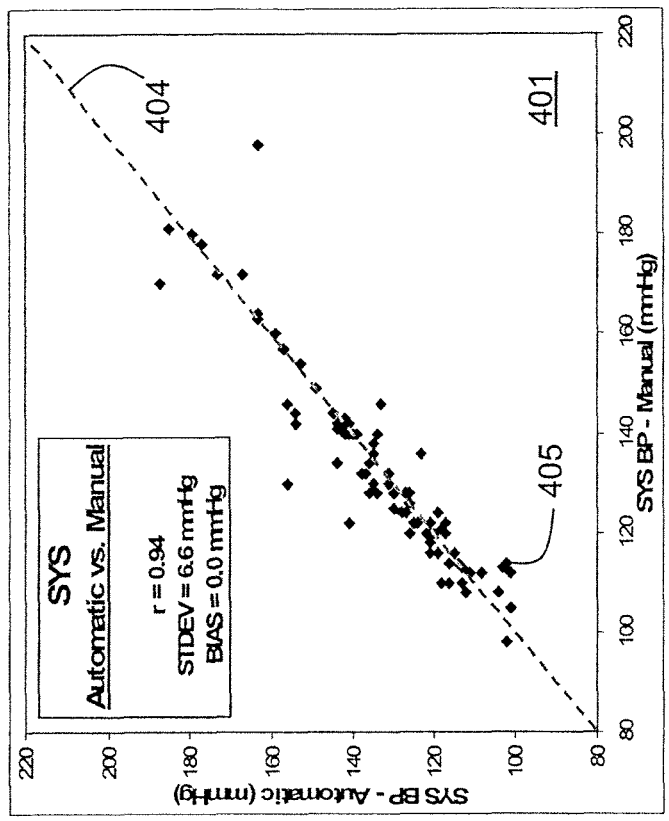
FIGS. 16A and 16B are graphs of, respectively, systolic blood pressure measured with the pressure-dependent measurement of the composite technique and a manual measurement, and systolic blood pressure measured with an automatic measurement and the manual measurement.
Figure 16A:
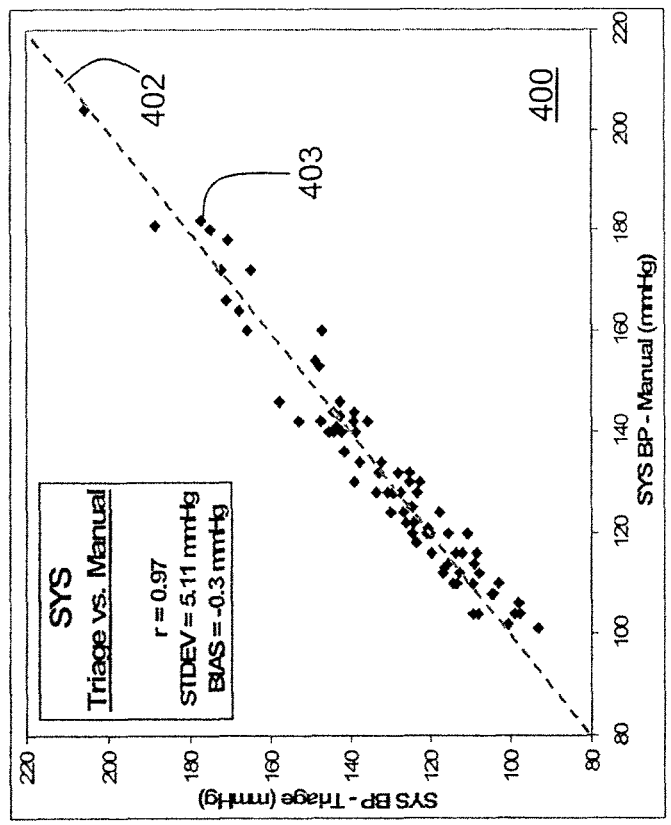
Figures 17A, 17B:
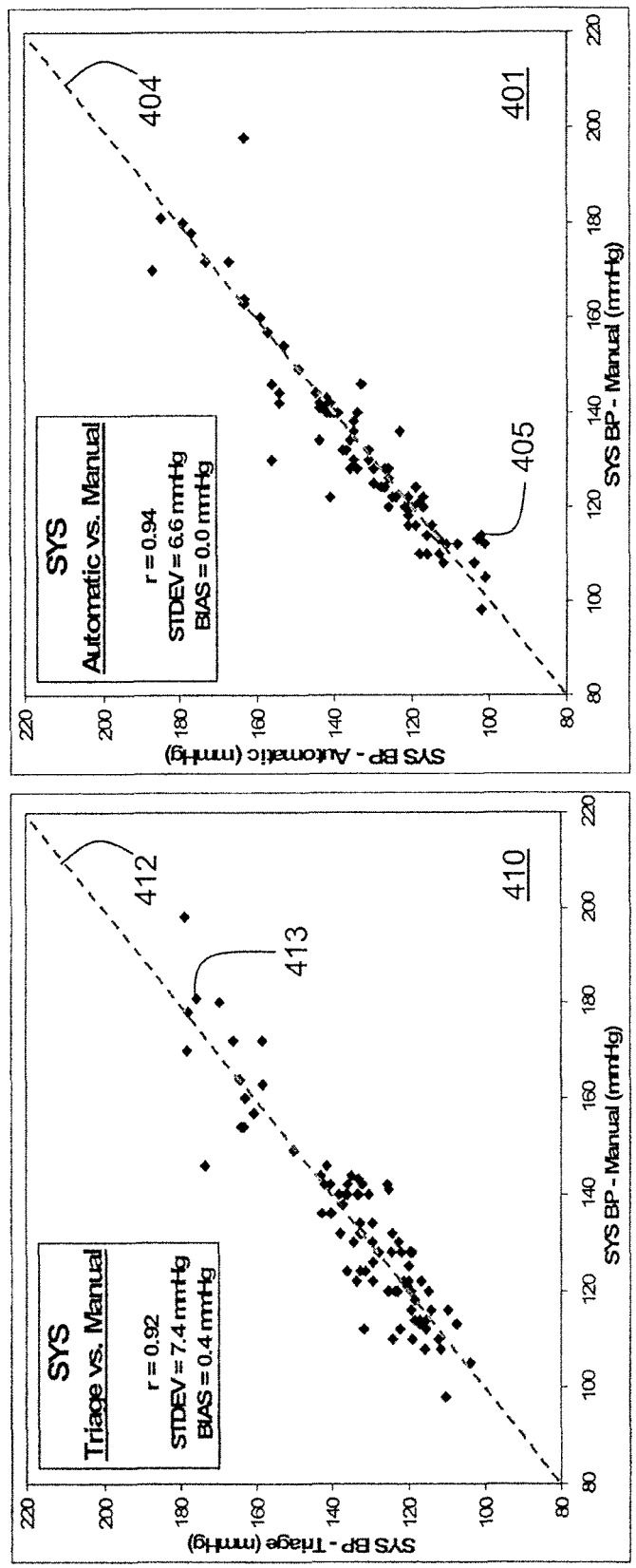
FIGS. 17A and 17B are graphs of, respectively, systolic blood pressure measured with the pressure-free measurement of the composite technique and a manual measurement, and systolic blood pressure measured with an automatic measurement and the manual measurement.
Figure 18B:
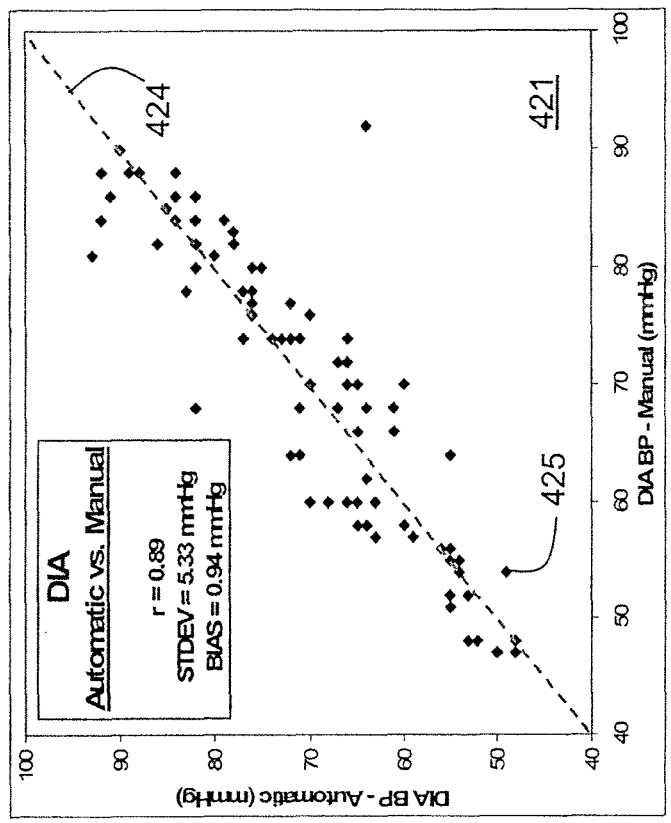
FIGS. 18A and 18B are graphs of, respectively, diastolic blood pressure measured with the pressure-free measurement of the composite technique and a manual measurement, and systolic blood pressure measured with an automatic measurement and the manual measurement.
Figure 18A:
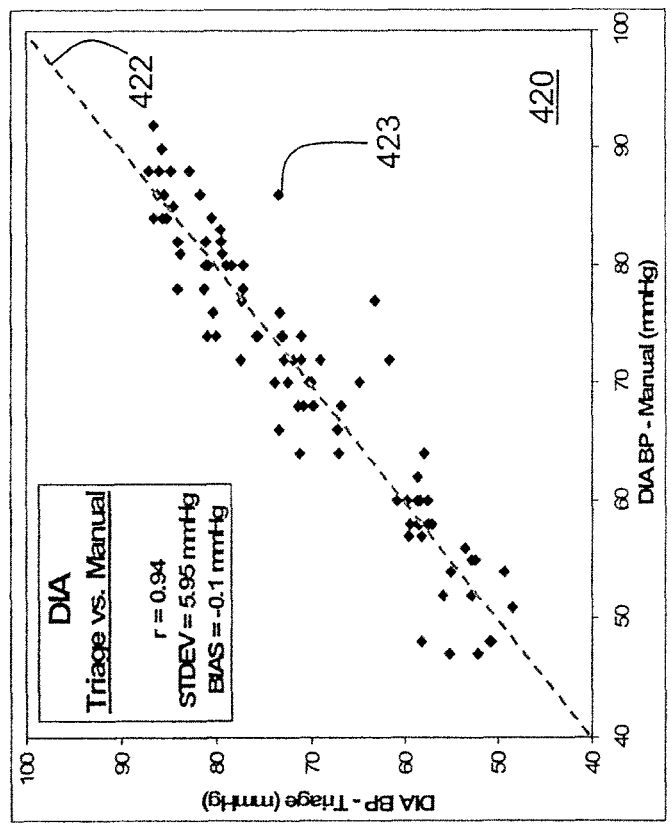

FIGS. 16A and 16B indicate the accuracy of the composite technique's pressure-dependent measurement during dialysis. Data for these figures were determined during the 15-minute intervals where simultaneous auscultatory, oscillometric, and composite measurements were made. The first graph in FIG. 16A shows the correlation between systolic blood pressure measured with the pressure-dependent measurement of the composite measurement (y-axis) and the auscultatory technique (x-axis). The second graph in the figure shows correlation between systolic blood pressure measured with the oscillometric technique (y-axis) and the auscultatory technique (x-axis). The correlation between the composite and auscultatory techniques ($r=0.97$) indicates the accuracy of this measurement, as does the bias of ($-0.3$ mmHg) and standard deviation (5.1 mmHg). The best-fit slope of the correlation was 1.01, which is identical to within experimental error to the ideal slope of 1. The correlation and standard deviation between the auscultatory and oscillometric techniques were similar (r=0.94, SD=±6.6 mmHg), while the bias was slightly better (0.0 mmHg) than the data from the composite technique, and the slope slightly deviated (0.93) from the ideal slope of 1.

FIGS. 17A, 17B, 18A, and 18B show how the composite technique's pressure-free measurements compared to measurements made with the auscultatory and oscillometric techniques. In this case, pressure-free measurements were determined a few seconds before the comparative measurements. In general, the agreements between the pressure-free and auscultatory measurements for systolic (FIGS. 17A and 17B; r=0.92; standard deviation=7.4 mmHg; bias=0.4 mmHg) and diastolic (FIGS. 18A and 18B; r=0.94; standard deviation=5.95 mmHg; bias=−0.1 mmHg) blood pressures were slightly worse than those for the pressure-dependent measurements, but still well within the AAMI/ANSI SP:10 guidelines mandated by the FDA (SD<8 mmHg; BIAS<|+/−5 mmHg|) for 510(k) approval. Errors are likely partially due to the fact that these measurements, unlike the pressure-dependent measurements, are made indirectly from different heart beats detected from the patient. Beat-to-beat variations in blood pressure, as well hemodynamic components unaffected by blood pressure but present in the pressure-free signal, likely contribute to this error.

FIGS. 20-23 show flow charts of specific algorithms used to calculate systolic ('SYS'), mean arterial ('MAP'), and diastolic ('DIA') blood pressure according to the above-described composite technique. The algorithms process optical, electrical, and pressure waveforms, each of which is measured by the body sensor as a function of time. The pressure waveform relates applied pressure and time, and thus processing this waveform in combination with the optical waveform yields an optical waveform that varies with pressure instead of time. This 'transformed' optical waveform is used in the algorithms shown in FIGS. 20 and 23. Technically, the pressure waveform includes a majority contribution from the pressure applied by the armband, and a minority contribution from heartbeat-induced pulsations occurring in the patient's arm due to the applied pressure. The contribution of these pulsations, shown for example in FIG. 8B, is therefore subtracted from the measured pressure waveform to determine the actual pressure applied by the pump.

Figure 20:
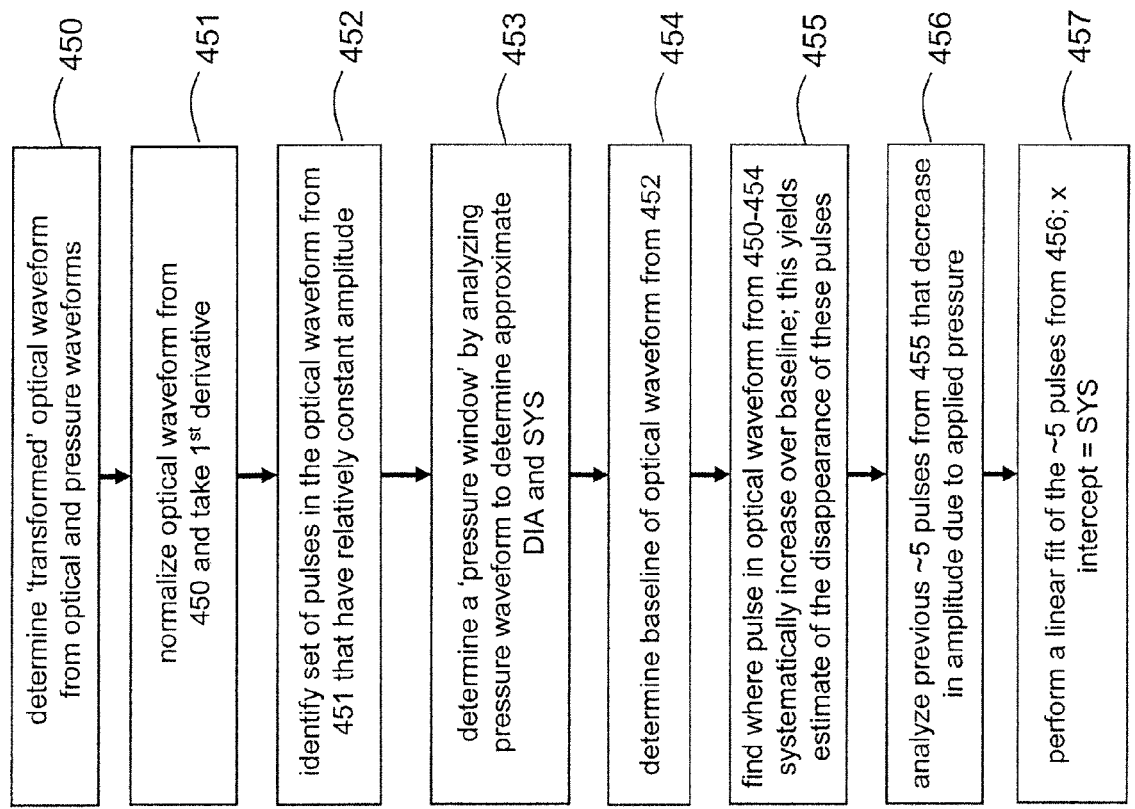
FIG. 20 is a flow chart showing an algorithm for calculating systolic blood pressure using the pressure-dependent measurement of the composite technique.

FIG. 20 shows a series of steps (450-457) of an algorithm for calculating SYS directly using the pressure-dependent measurement and the transformed, pressure-dependent optical waveform. The algorithm involves collecting optical, electrical, and pressure waveforms during a pressure-dependent measurement, and then determining the transformed optical waveform (step 450) as described above. The algorithm then 'normalizes' the optical waveform by dividing all the waveform's data points by a maximum amplitude, and then taking a first derivative of the normalized waveform (step 451). The normalization process removes an 'absolute' amplitude component from the waveform, and allows the algorithm to analyze relative changes in the optical pulses; the first derivative process removes any DC components from the waveform. The optical waveform collected during step 450 and analyzed during step 451 features a series of pulses, collected before the applied pressure reaches DIA, that have relatively constant amplitudes. In step 452, the algorithm then processes pulses in the waveform from step 451 to identify those having a relatively constant value (e.g. an amplitude variation of <10%); these pulse typically occur when the applied pressure is less than DIA. As the applied pressure ramps from DIA to MAP, the amplitude begins to decrease. In step 453, the algorithm analyzes the pressure waveform as described above to estimate DIA and SYS; these parameters represent boundaries of a 'pressure window' over which the optical waveform from steps 450-452 is analyzed. DIA and SYS are determined indirectly from a Gaussian envelope, similar to that shown in FIG. 9, which is derived from a filtered pressure waveform similar to that shown in FIG. 8B. In step 454, the algorithm determines the baseline of the optical waveform from step 452; this value is typically near 0. In step 455, the algorithm evaluates pulses in the optical waveform around a time corresponding to the estimated SYS value from step 453, and estimates the pressure at which these pulses disappear. In step 456, the algorithm analyzes the amplitudes of approximately 5 pulses occurring at pressures less than that determined in step 455; these amplitudes typically decrease in a systematic manner as the applied pressure approaches the patient's actual SYS. In step 457, the algorithm then fits the decaying amplitudes of these 5 pulses, with the x-intercept (i.e. the value of the x-axis at which the y-axis is zero) determined from the fit indicating SYS.

Figure 21:
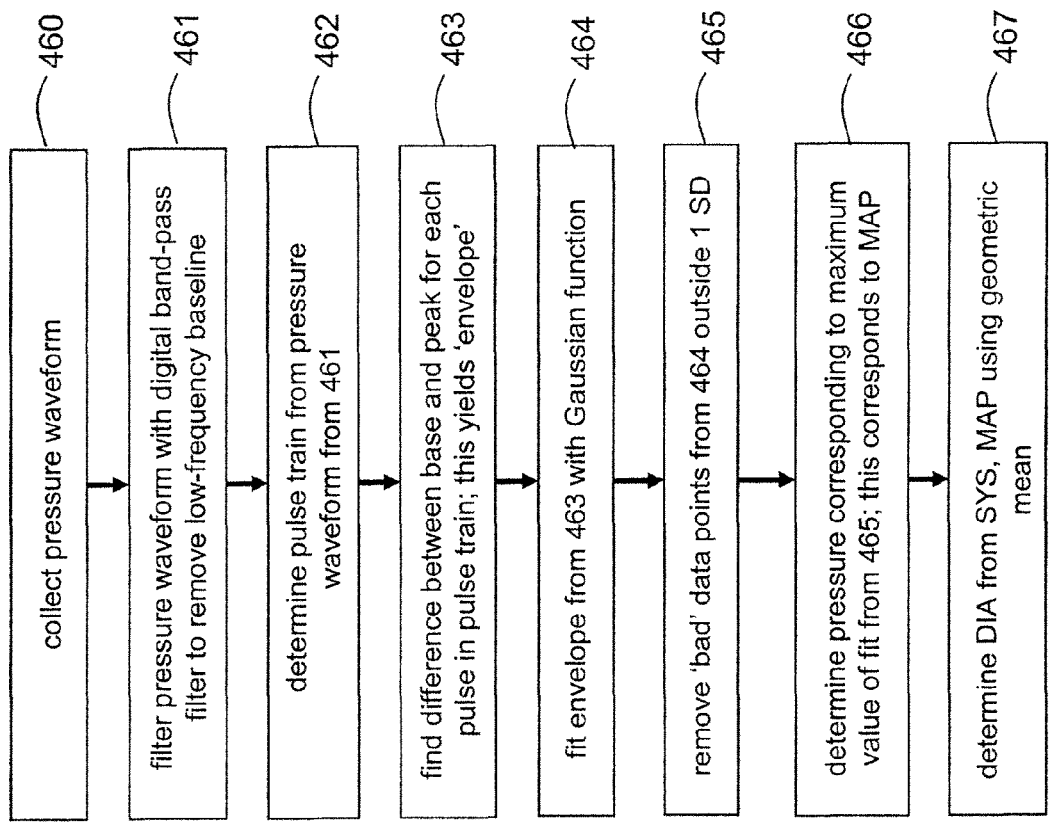
FIG. 21 is a flow chart showing an algorithm for calculating mean arterial blood pressure using the pressure-dependent measurement of the composite technique.

FIG. 21 describes an algorithm for calculating MAP and DIA using the pressure-dependent measurement. In this algorithm, the body sensor collects a pressure waveform (step 460), and then filters it with a band-pass filter to remove its low-frequency baseline and other unwanted noise (step 461). The filtered waveform includes a series of pulses, similar to that shown in FIG. 8B. The algorithm uses a conventional peak-detection algorithm to determine the base-to-peak amplitudes of these pulses (steps 462, 463); they typically form a pulse train characterized by a Gaussian envelope. In step 464, the algorithm fits the envelope with a Gaussian function (shown, for example, in Equation 2); a similar fit is shown in FIG. 9. The Gaussian function draws a smooth line through the data points corresponding to each pulse. Data points that differ from the fit by more than 1 standard deviation are removed (step 465), and the then algorithm determines MAP from the maximum value of the Gaussian fit (step 466). In step 467, the algorithm uses either Equation 3 or 4 to determine DIA from MAP determined during step 466, and SYS determined by the algorithm shown in FIG. 20.

Figure 22:
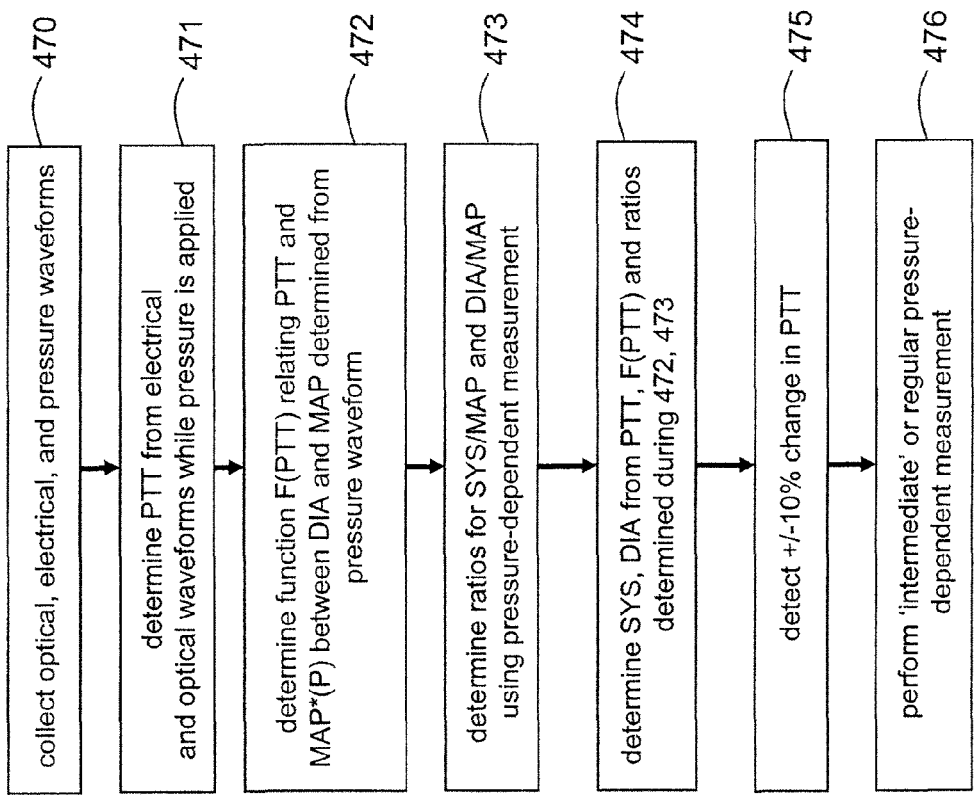
FIG. 22 is a flow chart showing an algorithm for calculating systolic and diastolic blood pressures using the pressure-free measurement of the composite technique.

FIG. 22 describes an algorithm for first 'calibrating' a PTT-based blood pressure measurement during a pressure-dependent measurement, and then determining SYS and DIA during a pressure-free measurement. The algorithm collects optical, electrical, and pressure waveforms (step 470) during a pressure-dependent measurement, and determines PTT from the optical and electrical waveforms while pressure is applied. The algorithm then determines the mathematical relationship 'F(PTT)' relating PTT and the pressure-dependent 'effective' MAP (MAP*(P)), calculated according to Equation 1. F(PTT) is determined while the applied pressure is between DIA and MAP, and is typically a linear equation, as indicated in FIG. 5A. Typically DIA and MAP are determined beforehand using the algorithm shown in FIG. 21. Using DIA and MAP values from this algorithm, and SYS values from the algorithm shown in FIG. 20, the algorithm then calculates ratios for SYS/MAP and DIA/MAP (step 473). These ratios are relatively constant for a range of blood pressure values. At this point the algorithm uses waveforms collected during a pressure-free measurement. In step 474 the algorithm measures PTT from the optical and electrical waveforms, and calculates SYS and DIA using F(PTT) (step 472) and the SYS/MAP and SYS/DIA ratios (step 473). If the algorithm detects a 10% change in blood pressure (step 475), it can initiate an intermediate or conventional pressure-dependent measurement (step 476).

Figure 23:
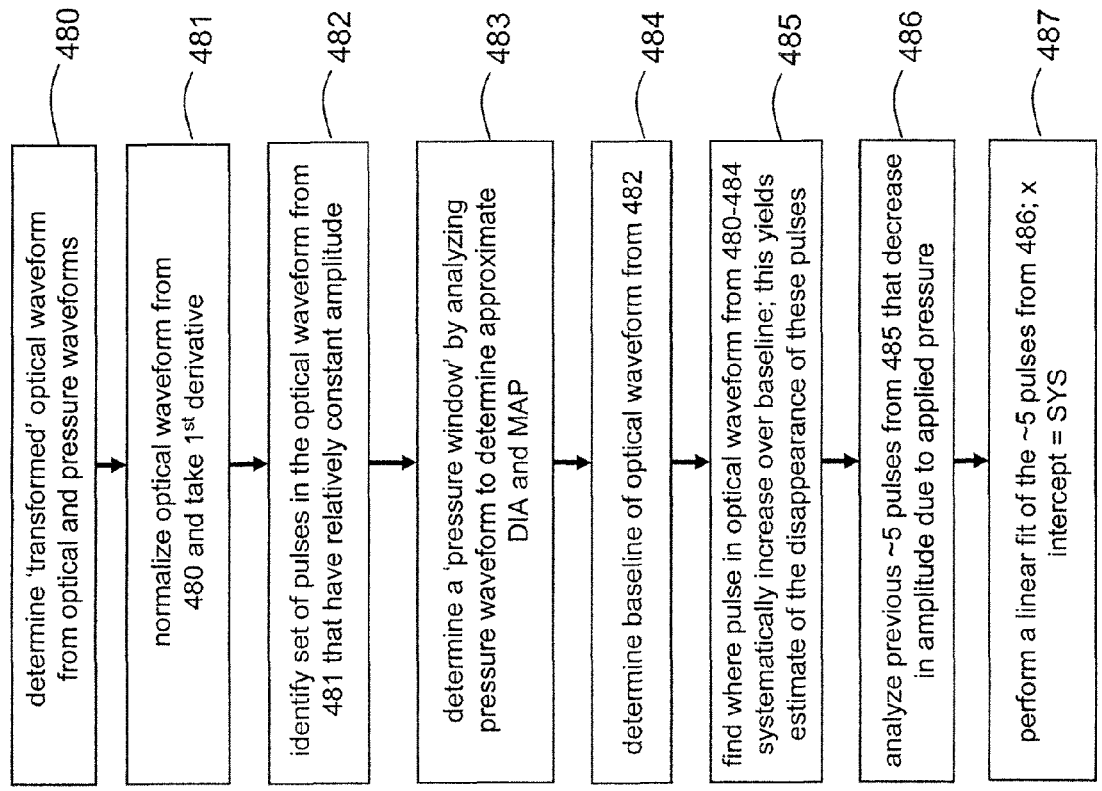
FIG. 23 is a flow chart showing an algorithm for calculating systolic blood pressure using an intermediate pressure-dependent measurement of the composite technique.

FIG. 23 describes an algorithm for determining SYS using an 'intermediate' pressure-dependent measurement. This algorithm is similar to that shown in FIG. 20, differing only in step 483. In this step a relatively low amount of pressure (no greater than MAP) is applied to the patient. This relatively low pressure reduces the amplitude of the optical pulses, but does not extinguish them, as is done for the algorithm shown in FIG. 20. But it also yields a sufficient number of data points that it is possible to generate a good estimate of SYS through a function (e.g. a linear function) fitted to those data points. The reduced optical pulses are then processed and fit (steps 484-487), as described with reference to FIG. 20, in order to estimate the x-intercept indicating SYS.

In addition to those methods described above, a number of alternative methods can be used to calculate blood pressure from the optical and electrical waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S.S.N; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S. Ser. No. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other techniques, such as conventional oscillometry, can be used to determine systolic blood pressure for the above-described algorithms.

In other embodiments, a variety of software configurations can be run on the monitor to give it a PDA-like functionality. These include, for example, Micro C OS®, Linux®, Microsoft Windows®, embOS, VxWorks, SymbianOS, QNX, OSE, BSD and its variants, FreeDOS, FreeRTOX, LynxOS, or eCOS and other embedded operating systems. The monitor can also run a software configuration that allows it to receive and send voice calls, text messages, or video streams received through the Internet or from the nation-wide wireless network it connects to. The barcode scanner described with reference to FIG. 13 can also be used to capture patient or medical professional identification information, or other such labeling. This information, for example, can be used to communicate with a patient in a hospital or at home. In other embodiments, the device can connect to an Internet-accessible website to download content, e.g., calibrations, software updates, text messages, and information describing medications, from an associated website. As described above, the device can connect to the website using both wired (e.g., USB port) or wireless (e.g., short or long-range wireless transceivers) means. In still other embodiments, 'alert' values corresponding to vital signs and the pager or cell phone number of a caregiver can be programmed into the device using its graphical user interface. If a patient's vital signs meet an alert criteria, software on the device can send a wireless 'page' to the caregiver, thereby alerting them to the patient's condition. For additional patient safety, a confirmation scheme can be implemented that alerts other individuals or systems until acknowledgment of the alert is received.

Still other embodiments are within the scope of the following claims.

What is claims is:

1. A system for monitoring a patient's vital signs, the system comprising:
   a pressure-delivery system for applying a variable pressure to the patient's arm;
   a pressure sensor for measuring a time-dependent pressure waveform representing the pressure applied to the patient's arm;
   an optical sensor configured to attach to the patient and generate a time-dependent optical waveform representing a flow of blood within the patient;
   an electrode system configured to attach to the patient and generate a time-dependent electrical waveform representing activity of the patient's heart; and
   a processing component programmed to: i) determine a pulse transit time when pressure is applied to the patient's arm by the pressure system, wherein pulse transit time is a measure of a separation in time of a first feature of the time-dependent electrical waveform and a second feature of the time-dependent optical waveform; ii) determine a variation in an amplitude of the optical waveform versus the pressure applied to the patient's arm; iii) fit a function to the variation in the amplitude of the optical waveform; iv) use the calibration value for the blood pressure parameter and a subsequently measured pulse transit time obtained for the patient when no pressure is applied to the patient's arm to determine the patient's blood pressure at that subsequent time.

2. The system of claim 1, wherein the blood pressure parameter is systolic blood pressure.

3. The system of claim 1, wherein the function is a linear function.

4. The system of claim 1, wherein the first feature of the time-dependent electrical waveform is a QRS complex and the second feature of the time-dependent optical waveform corresponds to a pressure pulse.

5. The system of claim 1, wherein the first feature of the time-dependent electrical waveform is a QRS complex and the second feature of the time-dependent optical waveform corresponds to a pressure pulse.

6. A method of monitoring a patient's vital sign, the method comprising:
- applying a variable pressure to the patient's arm;
- measuring a time-dependent pressure waveform representing the pressure applied to the patient's arm;
- sensing a time-dependent optical waveform representing a flow of blood within the patient;
- detecting a time-dependent electrical waveform representing activity of the patient's heart;
- determining a pulse transit time when applying pressure to the patient's arm, wherein pulse transit time is a measure of a separation in time of a first feature of the time-dependent electrical waveform and a second feature of the time-dependent optical waveform;
- determining a variation in pulse transit time with an amount of pressure applied to the patient's arm;
- determining a variation in an amplitude of the optical waveform versus the pressure applied to the patient's arm;
- fitting a function to the variation in the amplitude of the optical waveform;
- determining a calibration value for a blood pressure parameter from the fitted function and the variation in pulse transit time with the amount of pressure applied to the patient's arm; and
- using the calibration value for the blood pressure parameter and a subsequently measured pulse transit time obtained for the patient when no pressure is applied to the patients arm to determine the patient's blood pressure at that subsequent time.

7. A system for measuring a patient's vital signs, the system comprising:
- a pressure-delivery system for applying a variable pressure to the patient's arm;
- a pressure sensor for measuring a time-dependent pressure waveform representing the pressure applied to the patient's arm;
- an optical sensor configured to attach to the patient and generate a time-dependent optical waveform representing a flow of blood within the patient; and
- a processing component programmed to: i) determine a variation in an amplitude of the optical waveform versus the pressure applied to the patient's arm; ii) fit a function to the variation in the amplitude of the optical waveform; iii) determine a value for a blood pressure parameter form the fitted function, wherein the determined value is a systolic blood pressure for the patient; iv) determine a variation in pulse transit time with an amount of pressure applied to the patient's arm; and v) determine a calibration from the blood pressure parameter and the variation in pulse transit time with the amount of pressure applied to the patient's arm.

8. The system of claim 7, wherein the function is a linear function.

9. The system of claim 7, further comprising a housing unit that is configured to be worn in the patient's arm and wherein said housing unit contains the pressure-delivery system, the pressure sensor, and the processing component.

10. The system of claim 7, further comprising a housing unit that is configured to be worn in the patient's arm and wherein said housing unit contains the pressure-delivery system, the pressure sensor, and the processing component.

11. A method of measuring a patient's vital sign, the system comprising:
- applying a variable pressure to the patient's arm;
- measuring a time-dependent pressure waveform representing the pressure applied to the patient's arm;
- sensing a time-dependent optical waveform representing a flow of blood within the patient;
- determining a variation in an amplitude of the optical waveform versus the pressure applied to the patient's arm;
- fitting a function of the variation in the amplitude of the optical waveform versus the pressure applied to the patient's arm;
- determining a value for a blood pressure parameter from the fitted function, wherein the determined value is a systolic blood pressure for the patient;
- determining a variation in pulse transit time with an amount of pressure applied to the patient's arm; and
- determining a calibration from the blood pressure parameter and the variation in pulse transit time with the amount of pressure applied to the patient's arm.

* * * * *